United States Patent
Sahin et al.

(10) Patent No.: US 10,188,712 B2
(45) Date of Patent: Jan. 29, 2019

(54) TUMOR ANTIGENS FOR DETERMINING CANCER THERAPY

(71) Applicants: BioNTech AG, Mainz (DE); Tron—Translationale Onkologie An der Universitätsmedizin der Johannes Gutenberg-Universität Mainz Gemeinnützige GmbH, Mainz (DE)

(72) Inventors: Ugur Sahin, Mainz (DE); Claudia Paret, Mainz (DE); Kirsten Vormbrock, Mainz (DE); Christian Bender, Mainz (DE); Petra Simon, Mainz (DE); Christoph Hartmann, Frankfurt (DE); Stefanie Hubich, Mainz (DE); Thomas Bukur, Mainz (DE); Thorsten Litzenberger, Olsbrücken (DE)

(73) Assignees: BIONTECH AG (DE); TRON—Translationale Onkologie an der Universitätsmedizin Mainz Gemeinnützige GmbH (DE)

( * ) Notice: Subject to any disclaimer, the term of this patent is extended or adjusted under 35 U.S.C. 154(b) by 0 days.

(21) Appl. No.: 14/908,246

(22) PCT Filed: Jul. 30, 2014

(86) PCT No.: PCT/EP2014/066328
§ 371 (c)(1),
(2) Date: Jan. 28, 2016

(87) PCT Pub. No.: WO2015/014869
PCT Pub. Date: Feb. 5, 2015

(65) Prior Publication Data
US 2016/0175414 A1 Jun. 23, 2016

(51) Int. Cl.
*A61K 39/00* (2006.01)
*C07K 14/47* (2006.01)
*C12Q 1/6886* (2018.01)
*G01N 33/574* (2006.01)

(52) U.S. Cl.
CPC ...... *A61K 39/0011* (2013.01); *C07K 14/4748* (2013.01); *C12Q 1/6886* (2013.01); *G01N 33/57415* (2013.01); *G01N 33/57484* (2013.01); *A61K 2039/507* (2013.01); *A61K 2039/53* (2013.01); *A61K 2039/70* (2013.01); *C12Q 2600/106* (2013.01); *C12Q 2600/158* (2013.01); *C12Q 2600/16* (2013.01); *G01N 2333/47* (2013.01)

(58) Field of Classification Search
None
See application file for complete search history.

(56) References Cited

U.S. PATENT DOCUMENTS

2010/0120683 A1* 5/2010 Kessler ............ A61K 39/0011
514/21.6

FOREIGN PATENT DOCUMENTS

JP 2007126442 5/2007
WO WO-2008/080468 A1 7/2008
WO PCT/EP2014/066328 7/2014

OTHER PUBLICATIONS

Park et al. (Biochemica et Biophysica Acta, 1625: 173-182, 2003).*
Fukuyama et al. (Cancer Res, 66:4922-4928, 2006).*
Paret et al. (Oncotarget, 6(28): 25356-25367, 2015).*
Park et al. (Biochimica et Biophysica Acta, 1625: 173-182, 2003).*
Yasumoto et al. (Gen Thorac Cardiovasc Surg, 57:449-457, 2009).*
Bauer et al. (Cancer, 109(9): 1721-1728, 2007).*
International Search Report and Written Opinion dated Nov. 20, 2014 for application PCT/EP2014/066328, filed on Jul. 30, 2014 and published as WO 2015/014869 on Feb. 5, 2015 (Applicant—Biontech AG // Inventor—Sahin, et al.) (19 pages).
International Preliminary Report on Patentability dated Feb. 2, 2016 for application PCT/EP2014/066328, filed on Jul. 30, 2014 and published as WO 2015/014869 on Feb. 5, 2015 (Applicant—Biontech AG // Inventor—Sahin, et al.) (12 pages).
Fukuyama, et al., "Identification of a new cancer/germline gene, KK-LC-1, encoding an antigen recognized by autologous CTL induced on human lung adenocarcinoma", Cancer Research., vol. 66, No. 9, pp. 4922-4928.
Park, et al., "Identification and characterization of a novel cancer/testis antigen gene CAGE-1", Biochimica et Biophysica Acta, Gene Structure and Expression, vol. 1625, No. 2, Jan. 27, 2003 pp. 173-182.
Kessler, et al., "Efficient identification of novel HLA-A(*)0201-presented cytotoxic T lymphocyte epitopes in the widely expressed tumor antigen PRAME by proteasome-mediated digestion analysis", J. Exp. Med., vol. 193. No. 1, Jan. 1, 2001, pp. 73-88.
Kreiter, et al., "Tumor vaccination using messenger RNA: prospects of a future therapy", Current Opinions in Immunology, vol. 23, No. 3, Jun. 1, 2011, pp. 399-406.
Helftenbein, et al., "In silica strategy for detection of target candidates for antibody therapy of solid tumors", Gene, vol. 414, No. 1-2, May 15, 2008, pp. 76-84.
Sahin, et al., "Serological identification of human tumor antigens", Current Opinion in Immunology, vol. 9, No. 5, Oct. 1, 1997, pp. 709-716.
Sahin, et al., "Serological analysis of human tumor antigens: molecular definition and implications", Molecular Medicine Today, vol. 3, No. 8, Aug. 1, 1997, pp. 342-349.
Database EMBL [Online] Jun. 16, 1997 (Jun. 16, 1997), "Human DNA sequence from clone RP3-452H17 on chromosome Xq22.1-23 Contains the 3' end of the SLC6A14 gene for solute carrier family 6 (neurotransmitter transporter) member 14 and the gene for a novel protein (LOC203413)", retrieved from EBI accession No. EM STD:Z96810 (24 pages).
Database Geneseq [Online] Sep. 16, 2002 (Sep. 16, 2002), "Human prostate expression marker cDNA 25133", retrieved from EBI accession No. GSN:ABV25142 (2 pages).
Fratta, E. et al., "The biology of cancer testis antigens: Putative function, regulation and therapeutic potential", Molecular Oncology, 2011, vol. 5, p. 164-182.
Stagg, J. and Allard, B., Immunotherapeutic Approaches n Triple-Negative Breast Cancer: Latest Research and Clinical Prospects. Ther Adv Med Oncol. 2013; 5(3):169-81.

* cited by examiner

*Primary Examiner* — Nelson B Moseley, II
(74) *Attorney, Agent, or Firm* — Ballard Spahr LLP

(57) ABSTRACT

The present invention relates to the treatment of cancer, in particular breast cancer, particularly triple-negative breast cancer. More particularly, the invention concerns methods and means for cancer treatment involving a specific set of tumor antigens.

Figure 1:
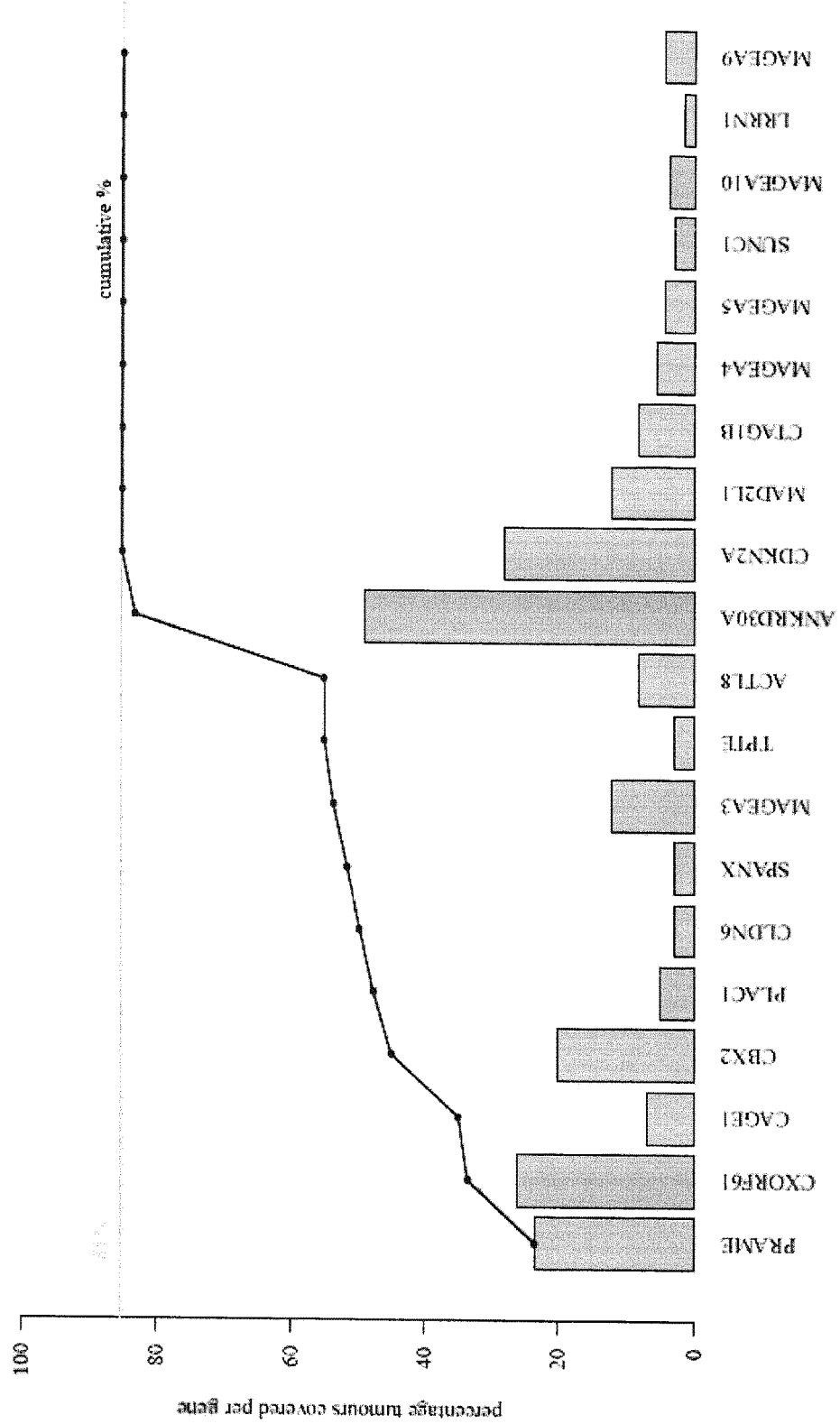

7 Claims, 17 Drawing Sheets
Specification includes a Sequence Listing.

Fig. 6A

SYFPEITHY-predicted HLA-A*0201 binding peptides

| Peptide | Sequence | Position | Score |
|---|---|---|---|
| CXORF61-A2-1 | KLVELEHTL | 90-98 | 27 |
| CXORF61-A2-2 | ILNNFPHSI | 66-74 | 25 |
| CXORF61-A2-3 | YILLASSIL | 4-12 | 24 |
| CXORF61-A2-4 | RILVNLSMV | 79-87 | 24 |
| CXORF61-A2-5 | LLASSILCA | 6-14 | 23 |
| CXORF61-A2-6 | NLSMVENKL | 83-91 | 23 |

Fig. 8 aattgtgaggtctgcgcgccctcagccgtacataaagcgggacaacacagaacttccagttacacc
aggcatcctggcccaaagtttccaaatccaggcggctagaggcccactgcttccaactaccagc
tgaggggtccgtccgagaaggaggagaggccgaagaggaaacatgaacttctatttactcct
agcgagcagcattcgtgtgccttgattgtcttctgaaatatcgccgctttcagagaaacactggcga
aatgtcatcaaattcaactgctcttgcactagtgagaccctctcttctggttaattaacagcaatacag
acaacaatcttgcagtctctcgggatatttaaataattcccactcaatagccaggc
agaagcgaatattggtaaacctcagtatggtggaaaacaagctggttgaactgaacatactctactt
agcaagggtttcagaggtgcatcacctcaccgaaatccacctaaaagctacacaggatgtaatgcc
agtggtggaaatcattaaagacacttgagtagattcatttgattgtgtttatactaaatgaattatt
tttttaagagggaggggggattccaagtcacatacaaaaatccagatacttaccaagtttcttatt
tatactttaagtaattgattacatatggctaaaatatactactgaggaaggaagcaca
atagagaaagaaaacagttcaaaagtttgttaacataaaaa

SEQUENCE LISTING

```
<160> NUMBER OF SEQ ID NOS: 46

<210> SEQ ID NO 1
<211> LENGTH: 15
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(3)
<223> OTHER INFORMATION: Portion of sequence repeated a times, wherein a
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: MISC_FEATURE
<222> LOCATION: (1)..(15)
<223> OTHER INFORMATION: a + b + c + d + e are different from 0 and
      preferably are 2 or more, 3 or more, 4 or more or 5 or more
<220> FEATURE:
<221> NAME/KEY: REPEAT
<222> LOCATION: (4)..(6)
<223> OTHER INFORMATION: Portion of sequence repeated b times, wherein b
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (7)..(9)
<223> OTHER INFORMATION: Portion of sequence repeated c times, wherein c
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (10)..(12)
<223> OTHER INFORMATION: Portion of sequence repeated d times, wherein d
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (13)..(15)
<223> OTHER INFORMATION: Portion of sequence repeated e times, wherein e
      is independently a number selected from 0, 1, 2, 3, 4, 5, 6, 7, 8,
      9, 10, 11, 12, 13, 14, 15, 16, 17, 18, 19, or 20
```

<400> SEQUENCE: 1

Gly Gly Ser Gly Ser Ser Gly Gly Ser Ser Gly Gly Ser Gly
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Linker sequence

<400> SEQUENCE: 2

Gly Gly Ser Gly Gly Gly Gly Ser Gly
1               5

<210> SEQ ID NO 3
<211> LENGTH: 113
<212> TYPE: PRT
<213> ORGANISM: Homo sapiens

<400> SEQUENCE: 3

Met Asn Phe Tyr Leu Leu Leu Ala Ser Ser Ile Leu Cys Ala Leu Ile
1               5                   10                  15

Val Phe Trp Lys Tyr Arg Arg Phe Gln Arg Asn Thr Gly Glu Met Ser
            20                  25                  30

Ser Asn Ser Thr Ala Leu Ala Leu Val Arg Pro Ser Ser Ser Gly Leu
        35                  40                  45

Ile Asn Ser Asn Thr Asp Asn Asn Leu Ala Val Tyr Asp Leu Ser Arg
    50                  55                  60

Asp Ile Leu Asn Asn Phe Pro His Ser Ile Ala Arg Gln Lys Arg Ile
65                  70                  75                  80

Leu Val Asn Leu Ser Met Val Glu Asn Lys Leu Val Glu Leu Glu His
                85                  90                  95

Thr Leu Leu Ser Lys Gly Phe Arg Gly Ala Ser Pro His Arg Lys Ser
                100                 105                 110

Thr

<210> SEQ ID NO 4
<211> LENGTH: 777
<212> TYPE: PRT
<213> ORGANISM: Homo sapiens

<400> SEQUENCE: 4

Met Asn Lys Asp Tyr Gln Lys Phe Trp Ser Ser Pro Ser Asp Pro Val
1               5                   10                  15

His Phe Glu Val Asp Thr Ser His Glu Lys Val Glu Ser Met Ser Glu
            20                  25                  30

Ser Asp Thr Met Asn Val Ser Asn Leu Ser Gln Gly Val Met Leu Ser
        35                  40                  45

His Ser Pro Ile Cys Met Glu Thr Thr Gly Thr Thr Cys Asp Leu Pro
    50                  55                  60

Gln Asn Glu Ile Lys Asn Phe Glu Arg Glu Asn Glu Tyr Glu Ser Thr
65                  70                  75                  80

Leu Cys Glu Asp Ala Tyr Gly Thr Leu Asp Asn Leu Leu Asn Asp Asn
                85                  90                  95

Asn Ile Glu Asn Tyr Ser Thr Asn Ala Leu Ile Gln Pro Val Asp Thr
                100                 105                 110

```
Ile Ser Ile Ser Ser Leu Arg Gln Phe Glu Thr Val Cys Lys Phe His
            115                 120                 125

Trp Val Glu Ala Phe Asp Asp Glu Met Thr Glu Lys Pro Glu Phe Gln
130                 135                 140

Ser Gln Val Tyr Asn Tyr Ala Lys Asp Asn Ile Lys Gln Asp Ser
145                 150                 155                 160

Phe Lys Glu Glu Asn Pro Met Glu Thr Ser Val Ser Ala Asn Thr Asp
                165                 170                 175

Gln Leu Gly Asn Glu Tyr Phe Arg Gln Pro Pro Arg Ser Pro Pro
                180                 185                 190

Leu Ile His Cys Ser Gly Glu Met Leu Lys Phe Thr Glu Lys Ser Leu
                195                 200                 205

Ala Lys Ser Ile Ala Lys Glu Ser Ala Leu Asn Pro Ser Gln Pro Pro
210                 215                 220

Ser Phe Leu Cys Lys Thr Ala Val Pro Ser Lys Glu Ile Gln Asn Tyr
225                 230                 235                 240

Gly Glu Ile Pro Glu Met Ser Val Ser Tyr Glu Lys Glu Val Thr Ala
                245                 250                 255

Glu Gly Val Glu Arg Pro Glu Ile Val Ser Thr Trp Ser Ser Ala Gly
                260                 265                 270

Ile Ser Trp Arg Ser Glu Ala Cys Arg Glu Asn Cys Glu Met Pro Asp
                275                 280                 285

Trp Glu Gln Ser Ala Glu Ser Leu Gln Pro Val Gln Glu Asp Met Ala
                290                 295                 300

Leu Asn Glu Val Leu Gln Lys Leu Lys His Thr Asn Arg Lys Gln Glu
305                 310                 315                 320

Val Arg Ile Gln Glu Leu Gln Cys Ser Asn Leu Tyr Leu Glu Lys Arg
                325                 330                 335

Val Lys Glu Leu Gln Met Lys Ile Thr Lys Gln Gln Val Phe Ile Asp
                340                 345                 350

Val Ile Asn Lys Leu Lys Glu Asn Val Glu Glu Leu Ile Glu Asp Lys
                355                 360                 365

Tyr Lys Ile Ile Leu Glu Lys Asn Asp Thr Lys Lys Thr Leu Gln Asn
370                 375                 380

Leu Glu Glu Val Leu Ala Asn Thr Gln Lys His Leu Gln Glu Ser Arg
385                 390                 395                 400

Asn Asp Lys Glu Met Leu Gln Leu Gln Phe Lys Lys Ile Lys Ala Asn
                405                 410                 415

Tyr Val Cys Leu Gln Glu Arg Tyr Met Thr Glu Met Gln Gln Lys Asn
                420                 425                 430

Lys Ser Val Ser Gln Tyr Leu Glu Met Asp Lys Thr Leu Ser Lys Lys
                435                 440                 445

Glu Glu Glu Val Glu Arg Leu Gln Gln Leu Lys Glu Leu Glu Lys
                450                 455                 460

Ala Thr Ala Ser Ala Leu Asp Leu Leu Lys Arg Glu Lys Glu Ala Gln
465                 470                 475                 480

Glu Gln Glu Phe Leu Ser Leu Gln Glu Glu Phe Gln Lys Leu Glu Lys
                485                 490                 495

Glu Asn Leu Glu Glu Arg Gln Lys Leu Lys Ser Arg Leu Glu Lys Leu
                500                 505                 510

Leu Thr Gln Val Arg Asn Leu Gln Phe Met Ser Glu Asn Glu Arg Thr
                515                 520                 525
```

-continued

```
Lys Asn Ile Lys Leu Gln Gln Gln Ile Asn Glu Val Lys Asn Glu Asn
            530                 535                 540
Ala Lys Leu Lys Gln Gln Val Ala Arg Ser Glu Glu Gln Asn Tyr Val
545                 550                 555                 560
Pro Lys Phe Glu Thr Ala Gln Leu Lys Asp Gln Leu Glu Val Leu
                565                 570                 575
Lys Ser Asp Ile Thr Lys Asp Thr Lys Thr Thr His Ser Asn Leu Leu
                580                 585                 590
Pro Asp Cys Ser Pro Cys Glu Arg Leu Asn Pro Ala Asp Ile Lys
                595                 600                 605
Arg Ala Ser Gln Leu Ala Ser Lys Met His Ser Leu Leu Ala Leu Met
610                 615                 620
Val Gly Leu Leu Thr Cys Gln Asp Ile Ile Asn Ser Asp Ala Glu His
625                 630                 635                 640
Phe Lys Glu Ser Glu Lys Val Ser Asp Ile Met Leu Gln Lys Leu Lys
                645                 650                 655
Ser Leu His Leu Lys Lys Lys Thr Leu Asp Lys Glu Val Ile Asp Cys
                660                 665                 670
Asp Ser Asp Glu Ala Lys Ser Ile Arg Asp Val Pro Thr Leu Leu Gly
                675                 680                 685
Ala Lys Leu Asp Lys Tyr His Ser Leu Asn Glu Glu Leu Asp Phe Leu
690                 695                 700
Val Thr Ser Tyr Glu Glu Ile Ile Glu Cys Ala Asp Gln Arg Leu Ala
705                 710                 715                 720
Ile Ser His Ser Gln Ile Ala His Leu Glu Glu Arg Asn Lys His Leu
                725                 730                 735
Glu Asp Leu Ile Arg Lys Pro Arg Glu Lys Ala Arg Lys Pro Arg Ser
                740                 745                 750
Lys Ser Leu Glu Asn His Pro Lys Ser Met Thr Met Met Pro Ala Leu
                755                 760                 765
Phe Lys Glu Asn Arg Asn Asp Leu Asp
                770                 775

<210> SEQ ID NO 5
<211> LENGTH: 641
<212> TYPE: PRT
<213> ORGANISM: Homo sapiens

<400> SEQUENCE: 5

Met Thr Glu Lys Pro Glu Phe Gln Ser Gln Val Tyr Asn Tyr Ala Lys
1               5                   10                  15
Asp Asn Asn Ile Lys Gln Asp Ser Phe Lys Glu Glu Asn Pro Met Glu
                20                  25                  30
Thr Ser Val Ser Ala Asn Thr Asp Gln Leu Gly Asn Glu Tyr Phe Arg
                35                  40                  45
Gln Pro Pro Pro Arg Ser Pro Leu Ile His Cys Ser Gly Glu Met
            50                  55                  60
Leu Lys Phe Thr Glu Lys Ser Leu Ala Lys Ser Ile Ala Lys Glu Ser
65                  70                  75                  80
Ala Leu Asn Pro Ser Gln Pro Ser Phe Leu Cys Lys Thr Ala Val
                85                  90                  95
Pro Ser Lys Glu Ile Gln Asn Tyr Gly Glu Ile Pro Glu Met Ser Val
                100                 105                 110
Ser Tyr Glu Lys Glu Val Thr Ala Glu Gly Val Glu Arg Pro Glu Ile
                115                 120                 125
```

```
Val Ser Thr Trp Ser Ser Ala Gly Ile Ser Trp Arg Ser Glu Ala Cys
    130                 135                 140

Arg Glu Asn Cys Glu Met Pro Asp Trp Glu Gln Ser Ala Glu Ser Leu
145                 150                 155                 160

Gln Pro Val Gln Glu Asp Met Ala Leu Asn Glu Val Leu Gln Lys Leu
                165                 170                 175

Lys His Thr Asn Arg Lys Gln Glu Val Arg Ile Gln Glu Leu Gln Cys
            180                 185                 190

Ser Asn Leu Tyr Leu Glu Lys Arg Val Lys Glu Leu Gln Met Lys Ile
        195                 200                 205

Thr Lys Gln Gln Val Phe Ile Asp Val Ile Asn Lys Leu Lys Glu Asn
210                 215                 220

Val Glu Glu Leu Ile Glu Asp Lys Tyr Lys Ile Ile Leu Glu Lys Asn
225                 230                 235                 240

Asp Thr Lys Lys Thr Leu Gln Asn Leu Glu Glu Val Leu Ala Asn Thr
                245                 250                 255

Gln Lys His Leu Gln Glu Ser Arg Asn Asp Lys Glu Met Leu Gln Leu
            260                 265                 270

Gln Phe Lys Lys Ile Lys Ala Asn Tyr Val Cys Leu Gln Glu Arg Tyr
        275                 280                 285

Met Thr Glu Met Gln Gln Lys Asn Lys Ser Val Ser Gln Tyr Leu Glu
290                 295                 300

Met Asp Lys Thr Leu Ser Lys Lys Glu Glu Val Glu Arg Leu Gln
305                 310                 315                 320

Gln Leu Lys Lys Glu Leu Glu Lys Ala Thr Ala Ser Ala Leu Asp Leu
                325                 330                 335

Leu Lys Arg Glu Lys Glu Ala Gln Glu Gln Glu Phe Leu Ser Leu Gln
            340                 345                 350

Glu Glu Phe Gln Lys Leu Glu Lys Glu Asn Leu Glu Glu Arg Gln Lys
        355                 360                 365

Leu Lys Ser Arg Leu Glu Lys Leu Leu Thr Gln Val Arg Asn Leu Gln
370                 375                 380

Phe Met Ser Glu Asn Glu Arg Thr Lys Asn Ile Lys Leu Gln Gln Gln
385                 390                 395                 400

Ile Asn Glu Val Lys Asn Glu Asn Ala Lys Leu Lys Gln Gln Val Ala
                405                 410                 415

Arg Ser Glu Glu Gln Asn Tyr Val Pro Lys Phe Glu Thr Ala Gln Leu
            420                 425                 430

Lys Asp Gln Leu Glu Glu Val Leu Lys Ser Asp Ile Thr Lys Asp Thr
        435                 440                 445

Lys Thr Thr His Ser Asn Leu Leu Pro Asp Cys Ser Pro Cys Glu Glu
450                 455                 460

Arg Leu Asn Pro Ala Asp Ile Lys Arg Ala Ser Gln Leu Ala Ser Lys
465                 470                 475                 480

Met His Ser Leu Leu Ala Leu Met Val Gly Leu Leu Thr Cys Gln Asp
                485                 490                 495

Ile Ile Asn Ser Asp Ala Glu His Phe Lys Glu Ser Glu Lys Val Ser
            500                 505                 510

Asp Ile Met Leu Gln Lys Leu Lys Ser Leu His Leu Lys Lys Lys Thr
        515                 520                 525

Leu Asp Lys Glu Val Ile Asp Cys Asp Ser Asp Glu Ala Lys Ser Ile
530                 535                 540
```

Arg Asp Val Pro Thr Leu Leu Gly Ala Lys Leu Asp Lys Tyr His Ser
545                 550                 555                 560

Leu Asn Glu Glu Leu Asp Phe Leu Val Thr Ser Tyr Glu Glu Ile Ile
                565                 570                 575

Glu Cys Ala Asp Gln Arg Leu Ala Ile Ser His Ser Gln Ile Ala His
            580                 585                 590

Leu Glu Glu Arg Asn Lys His Leu Glu Asp Leu Ile Arg Lys Pro Arg
        595                 600                 605

Glu Lys Ala Arg Lys Pro Arg Ser Lys Ser Leu Glu Asn His Pro Lys
    610                 615                 620

Ser Met Thr Met Met Pro Ala Leu Phe Lys Glu Asn Arg Asn Asp Leu
625                 630                 635                 640

Asp

<210> SEQ ID NO 6
<211> LENGTH: 824
<212> TYPE: PRT
<213> ORGANISM: Homo sapiens

<400> SEQUENCE: 6

Met Asn Lys Asp Tyr Gln Lys Phe Trp Ser Ser Pro Ser Asp Pro Val
1               5                   10                  15

His Phe Glu Val Asp Thr Ser His Glu Lys Val Glu Ser Met Ser Glu
            20                  25                  30

Ser Asp Thr Met Asn Val Ser Asn Leu Ser Gln Gly Val Met Leu Ser
        35                  40                  45

His Ser Pro Ile Cys Met Glu Thr Thr Gly Thr Thr Cys Asp Leu Pro
50                  55                  60

Gln Asn Glu Ile Lys Asn Phe Glu Arg Glu Asn Glu Tyr Glu Ser Thr
65                  70                  75                  80

Leu Cys Glu Asp Ala Tyr Gly Thr Leu Asp Asn Leu Leu Asn Asp Asn
                85                  90                  95

Asn Ile Glu Asn Tyr Ser Thr Asn Ala Leu Ile Gln Pro Val Asp Thr
            100                 105                 110

Ile Ser Ile Ser Ser Leu Arg Gln Phe Glu Thr Val Cys Lys Phe His
        115                 120                 125

Trp Val Glu Ala Phe Asp Asp Glu Met Thr Glu Lys Pro Glu Phe Gln
130                 135                 140

Ser Gln Val Tyr Asn Tyr Ala Lys Asp Asn Asn Ile Lys Gln Asp Ser
145                 150                 155                 160

Phe Lys Glu Glu Asn Pro Met Glu Thr Ser Val Ser Ala Asn Thr Asp
                165                 170                 175

Gln Leu Gly Asn Glu Tyr Phe Arg Gln Pro Pro Arg Ser Pro Pro
            180                 185                 190

Leu Ile His Cys Ser Gly Glu Met Leu Lys Phe Thr Glu Lys Ser Leu
        195                 200                 205

Ala Lys Ser Ile Ala Lys Glu Ser Ala Leu Asn Pro Ser Gln Pro Pro
210                 215                 220

Ser Phe Leu Cys Lys Thr Ala Val Pro Ser Lys Glu Ile Gln Asn Tyr
225                 230                 235                 240

Gly Glu Ile Pro Glu Met Ser Val Ser Tyr Glu Lys Glu Val Thr Ala
                245                 250                 255

Glu Gly Val Glu Arg Pro Glu Ile Val Ser Thr Trp Ser Ser Ala Gly
            260                 265                 270

-continued

```
Ile Ser Trp Arg Ser Glu Ala Cys Arg Glu Asn Cys Glu Met Pro Asp
            275                 280                 285
Trp Glu Gln Ser Ala Glu Ser Leu Gln Pro Val Gln Glu Asp Met Ala
290                 295                 300
Leu Asn Glu Val Leu Gln Lys Leu Lys His Thr Asn Arg Lys Gln Glu
305                 310                 315                 320
Val Arg Ile Gln Glu Leu Gln Cys Ser Asn Leu Tyr Leu Glu Lys Arg
                325                 330                 335
Val Lys Glu Leu Gln Met Lys Ile Thr Lys Gln Val Phe Ile Asp
                340                 345                 350
Val Ile Asn Lys Leu Lys Glu Asn Val Glu Glu Leu Ile Glu Asp Lys
            355                 360                 365
Tyr Lys Ile Ile Leu Glu Lys Asn Asp Thr Lys Thr Leu Gln Asn
370                 375                 380
Leu Glu Glu Val Leu Ala Asn Thr Gln Lys His Leu Gln Glu Ser Arg
385                 390                 395                 400
Asn Asp Lys Glu Met Leu Gln Leu Gln Phe Lys Lys Ile Lys Ala Asn
                405                 410                 415
Tyr Val Cys Leu Gln Glu Arg Tyr Met Thr Glu Met Gln Gln Lys Asn
                420                 425                 430
Lys Ser Val Ser Gln Tyr Leu Glu Met Asp Lys Thr Leu Ser Lys Lys
            435                 440                 445
Glu Glu Glu Val Glu Arg Leu Gln Leu Lys Lys Glu Leu Glu Lys
            450                 455                 460
Ala Thr Ala Ser Ala Leu Asp Leu Leu Lys Arg Glu Lys Glu Ala Gln
465                 470                 475                 480
Glu Gln Glu Phe Leu Ser Leu Gln Glu Glu Phe Gln Lys Leu Glu Lys
                485                 490                 495
Glu Asn Leu Glu Glu Arg Gln Lys Leu Lys Ser Arg Leu Glu Lys Leu
            500                 505                 510
Leu Thr Gln Val Arg Asn Leu Gln Phe Met Ser Glu Asn Glu Arg Thr
            515                 520                 525
Lys Asn Ile Lys Leu Gln Gln Gln Ile Asn Glu Val Lys Asn Glu Asn
530                 535                 540
Ala Lys Leu Lys Gln Gln Val Ala Arg Ser Glu Glu Gln Asn Tyr Val
545                 550                 555                 560
Pro Lys Phe Glu Thr Ala Gln Leu Lys Asp Gln Leu Glu Glu Val Leu
                565                 570                 575
Lys Ser Asp Ile Thr Lys Asp Thr Lys Thr Thr His Ser Asn Leu Leu
            580                 585                 590
Pro Asp Cys Ser Pro Cys Glu Glu Arg Leu Asn Pro Ala Asp Ile Lys
            595                 600                 605
Arg Ala Ser Gln Leu Ala Ser Lys Met His Ser Leu Leu Ala Leu Met
610                 615                 620
Val Gly Leu Leu Thr Cys Gln Asp Ile Ile Asn Ser Asp Ala Glu His
625                 630                 635                 640
Phe Lys Glu Ser Glu Lys Val Ser Asp Ile Met Leu Gln Lys Leu Lys
                645                 650                 655
Ser Leu His Leu Lys Lys Lys Thr Leu Asp Lys Glu Leu Leu Lys His
                660                 665                 670
Lys Asp Arg Ile Thr Thr Phe Arg Glu Leu Ile Ala Lys Glu Lys Ala
            675                 680                 685
```

```
Phe Gln Asp His Ala Ile Lys Val Ile Asp Cys Asp Ser Asp Glu Ala
    690             695                 700
Lys Ser Ile Arg Asp Val Pro Thr Leu Leu Gly Ala Lys Leu Asp Lys
705             710                 715                 720
Tyr His Ser Leu Asn Glu Glu Leu Asp Phe Leu Val Thr Ser Tyr Glu
                725                 730                 735
Glu Ile Ile Glu Cys Ala Asp Gln Arg Leu Ala Ile Ser His Ser Gln
                740                 745                 750
Ile Ala His Leu Glu Glu Arg Asn Lys His Leu Glu Asp Leu Ile Arg
                755                 760                 765
Lys Pro Arg Glu Lys Ala Arg Lys Pro Arg Ser Lys Ser Leu Glu Asn
770             775                 780
His Pro Lys Ser Met Thr Met Leu Ala Tyr Asn Leu Tyr Ile Phe Ile
785             790                 795                 800
Gly Tyr Arg Leu Gly Ala Val Ala Asp Ala Cys Asn Pro Ser Thr Leu
                805                 810                 815
Gly Gly Arg Gly Gly Trp Ile Thr
                820

<210> SEQ ID NO 7
<211> LENGTH: 700
<212> TYPE: PRT
<213> ORGANISM: Homo sapiens

<400> SEQUENCE: 7

Met Asn Lys Asp Tyr Gln Lys Phe Trp Ser Ser Pro Ser Asp Pro Val
1               5                   10                  15
His Phe Glu Val Asp Thr Ser His Glu Lys Val Glu Ser Met Ser Glu
                20                  25                  30
Ser Asp Thr Met Asn Val Ser Asn Leu Ser Gln Gly Val Met Leu Ser
                35                  40                  45
His Ser Pro Ile Cys Met Glu Thr Thr Gly Thr Thr Cys Asp Leu Pro
50                  55                  60
Gln Asn Glu Ile Lys Asn Phe Glu Arg Glu Asn Glu Tyr Glu Ser Thr
65                  70                  75                  80
Leu Cys Glu Asp Ala Tyr Gly Thr Leu Asp Asn Leu Leu Asn Asp Asn
                85                  90                  95
Asn Ile Glu Asn Tyr Ser Thr Asn Ala Leu Ile Gln Pro Val Asp Thr
                100                 105                 110
Ile Ser Ile Ser Ser Leu Arg Gln Phe Glu Thr Val Cys Lys Phe His
                115                 120                 125
Trp Val Glu Ala Phe Asp Asp Glu Met Thr Glu Lys Pro Glu Phe Gln
                130                 135                 140
Ser Gln Val Tyr Asn Tyr Ala Lys Asp Asn Ile Lys Gln Asp Ser
145             150                 155                 160
Phe Lys Glu Glu Asn Pro Met Glu Thr Ser Val Ser Ala Asn Thr Asp
                165                 170                 175
Gln Leu Gly Asn Glu Tyr Phe Arg Gln Pro Pro Arg Ser Pro Pro
                180                 185                 190
Leu Ile His Cys Ser Gly Glu Met Leu Lys Phe Thr Glu Lys Ser Leu
                195                 200                 205
Ala Lys Ser Ile Ala Lys Glu Ser Ala Leu Asn Pro Ser Gln Pro Pro
210                 215                 220
Ser Phe Leu Cys Lys Thr Ala Val Pro Ser Lys Glu Ile Gln Asn Tyr
225                 230                 235                 240
```

```
Gly Glu Ile Pro Glu Met Ser Val Ser Tyr Glu Lys Glu Val Thr Ala
                245                 250                 255
Glu Gly Val Glu Arg Pro Glu Ile Val Ser Thr Trp Ser Ser Ala Gly
            260                 265                 270
Ile Ser Trp Arg Ser Glu Ala Cys Arg Glu Asn Cys Glu Met Pro Asp
        275                 280                 285
Trp Glu Gln Ser Ala Glu Ser Leu Gln Pro Val Gln Glu Asp Met Ala
    290                 295                 300
Leu Asn Glu Val Leu Gln Lys Leu Lys His Thr Asn Arg Lys Gln Glu
305                 310                 315                 320
Val Arg Ile Gln Glu Leu Gln Cys Ser Asn Leu Tyr Leu Glu Lys Arg
                325                 330                 335
Val Lys Glu Leu Gln Met Lys Ile Thr Lys Gln Gln Val Phe Ile Asp
            340                 345                 350
Val Ile Asn Lys Leu Lys Glu Asn Val Glu Glu Leu Ile Glu Asp Lys
        355                 360                 365
Tyr Lys Ile Ile Leu Glu Lys Asn Asp Thr Lys Thr Leu Gln Asn
    370                 375                 380
Leu Glu Glu Val Leu Ala Asn Thr Gln Lys His Leu Gln Glu Ser Arg
385                 390                 395                 400
Asn Asp Lys Glu Met Leu Gln Leu Gln Phe Lys Lys Ile Lys Ala Asn
                405                 410                 415
Tyr Val Cys Leu Gln Glu Arg Tyr Met Thr Glu Met Gln Lys Asn
            420                 425                 430
Lys Ser Val Ser Gln Tyr Leu Glu Met Asp Lys Thr Leu Ser Lys Lys
        435                 440                 445
Glu Glu Glu Val Glu Arg Leu Gln Leu Lys Lys Glu Leu Glu Lys
    450                 455                 460
Ala Thr Ala Ser Ala Leu Asp Leu Leu Lys Arg Glu Lys Glu Ala Gln
465                 470                 475                 480
Glu Gln Glu Phe Leu Ser Leu Gln Glu Phe Gln Lys Leu Glu Lys
                485                 490                 495
Glu Asn Leu Glu Glu Arg Gln Lys Leu Lys Ser Arg Leu Glu Lys Leu
            500                 505                 510
Leu Thr Gln Val Arg Asn Leu Gln Phe Met Ser Glu Asn Glu Arg Thr
        515                 520                 525
Lys Asn Ile Lys Leu Gln Gln Gln Ile Asn Glu Val Lys Asn Glu Asn
    530                 535                 540
Ala Lys Leu Lys Gln Gln Val Ala Arg Ser Glu Glu Gln Asn Tyr Val
545                 550                 555                 560
Pro Lys Phe Glu Thr Ala Gln Leu Lys Asp Gln Leu Glu Glu Val Leu
                565                 570                 575
Lys Ser Asp Ile Thr Lys Asp Thr Lys Thr Thr His Ser Asn Leu Leu
            580                 585                 590
Pro Asp Cys Ser Pro Cys Glu Glu Arg Leu Asn Pro Ala Asp Ile Lys
        595                 600                 605
Arg Ala Ser Gln Leu Ala Ser Lys Met His Ser Leu Leu Ala Leu Met
    610                 615                 620
Val Gly Leu Leu Thr Cys Gln Asp Ile Ile Asn Ser Asp Ala Glu His
625                 630                 635                 640
Phe Lys Glu Ser Glu Lys Val Ser Asp Ile Met Leu Gln Lys Leu Lys
                645                 650                 655
```

```
Ser Leu His Leu Lys Lys Lys Thr Leu Asp Lys Glu Leu Leu Lys His
            660                 665                 670

Lys Asp Arg Ile Thr Thr Phe Arg Glu Leu Ile Ala Lys Glu Lys Ala
        675                 680                 685

Phe Gln Asp His Ala Ile Lys Val Phe Gln Gly Val
    690                 695                 700

<210> SEQ ID NO 8
<211> LENGTH: 839
<212> TYPE: PRT
<213> ORGANISM: Homo sapiens

<400> SEQUENCE: 8

Met Asn Lys Asp Tyr Gln Lys Phe Trp Ser Ser Pro Ser Asp Pro Val
1               5                   10                  15

His Phe Glu Val Asp Thr Ser His Glu Lys Val Glu Ser Met Ser Glu
            20                  25                  30

Ser Asp Thr Met Asn Val Ser Asn Leu Ser Gln Gly Val Met Leu Ser
        35                  40                  45

His Ser Pro Ile Cys Met Glu Thr Thr Gly Thr Thr Cys Asp Leu Pro
50                  55                  60

Gln Asn Glu Ile Lys Asn Phe Glu Arg Glu Asn Glu Tyr Glu Ser Thr
65                  70                  75                  80

Leu Cys Glu Asp Ala Tyr Gly Thr Leu Asp Asn Leu Leu Asn Asp Asn
                85                  90                  95

Asn Ile Glu Asn Tyr Ser Thr Asn Ala Leu Ile Gln Pro Val Asp Thr
            100                 105                 110

Ile Ser Ile Ser Ser Leu Arg Gln Phe Glu Thr Val Cys Lys Phe His
        115                 120                 125

Trp Val Glu Ala Phe Asp Asp Glu Met Thr Glu Lys Pro Glu Phe Gln
    130                 135                 140

Ser Gln Val Tyr Asn Tyr Ala Lys Asp Asn Asn Ile Lys Gln Asp Ser
145                 150                 155                 160

Phe Lys Glu Glu Asn Pro Met Glu Thr Ser Val Ser Ala Asn Thr Asp
                165                 170                 175

Gln Leu Gly Asn Glu Tyr Phe Arg Gln Pro Pro Arg Ser Pro Pro
            180                 185                 190

Leu Ile His Cys Ser Gly Glu Met Leu Lys Phe Thr Glu Lys Ser Leu
        195                 200                 205

Ala Lys Ser Ile Ala Lys Glu Ser Ala Leu Asn Pro Ser Gln Pro Pro
    210                 215                 220

Ser Phe Leu Cys Lys Thr Ala Val Pro Ser Lys Glu Ile Gln Asn Tyr
225                 230                 235                 240

Gly Glu Ile Pro Glu Met Ser Val Ser Tyr Lys Glu Val Thr Ala
                245                 250                 255

Glu Gly Val Glu Arg Pro Glu Ile Val Ser Thr Trp Ser Ser Ala Gly
            260                 265                 270

Ile Ser Trp Arg Ser Glu Ala Cys Arg Glu Asn Cys Glu Met Pro Asp
        275                 280                 285

Trp Glu Gln Ser Ala Glu Ser Leu Gln Pro Val Gln Glu Asp Met Ala
    290                 295                 300

Leu Asn Glu Val Leu Gln Lys Leu Lys His Thr Asn Arg Lys Gln Glu
305                 310                 315                 320

Val Arg Ile Gln Glu Leu Gln Cys Ser Asn Leu Tyr Leu Glu Lys Arg
                325                 330                 335
```

-continued

```
Val Lys Glu Leu Gln Met Lys Ile Thr Lys Gln Gln Val Phe Ile Asp
                340                 345                 350

Val Ile Asn Lys Leu Lys Glu Asn Val Glu Glu Leu Ile Glu Asp Lys
            355                 360                 365

Tyr Lys Ile Ile Leu Glu Lys Asn Asp Thr Lys Lys Thr Leu Gln Asn
        370                 375                 380

Leu Glu Glu Val Leu Ala Asn Thr Gln Lys His Leu Gln Glu Ser Arg
385                 390                 395                 400

Asn Asp Lys Glu Met Leu Gln Leu Gln Phe Lys Lys Ile Lys Ala Asn
                405                 410                 415

Tyr Val Cys Leu Gln Glu Arg Tyr Met Thr Glu Met Gln Gln Lys Asn
            420                 425                 430

Lys Ser Val Ser Gln Tyr Leu Glu Met Asp Lys Thr Leu Ser Lys Lys
        435                 440                 445

Glu Glu Glu Val Glu Arg Leu Gln Gln Leu Lys Lys Glu Leu Glu Lys
450                 455                 460

Ala Thr Ala Ser Ala Leu Asp Leu Leu Lys Arg Glu Lys Glu Ala Gln
465                 470                 475                 480

Glu Gln Glu Phe Leu Ser Leu Gln Glu Phe Gln Lys Leu Glu Lys
                485                 490                 495

Glu Asn Leu Glu Glu Arg Gln Lys Leu Lys Ser Arg Leu Glu Lys Leu
            500                 505                 510

Leu Thr Gln Val Arg Asn Leu Gln Phe Met Ser Glu Asn Glu Arg Thr
        515                 520                 525

Lys Asn Ile Lys Leu Gln Gln Gln Ile Asn Glu Val Lys Asn Glu Asn
530                 535                 540

Ala Lys Leu Lys Gln Gln Val Ala Arg Ser Glu Gln Asn Tyr Val
545                 550                 555                 560

Pro Lys Phe Glu Thr Ala Gln Leu Lys Asp Gln Leu Glu Glu Val Leu
                565                 570                 575

Lys Ser Asp Ile Thr Lys Asp Thr Lys Thr Thr His Ser Asn Leu Leu
            580                 585                 590

Pro Asp Cys Ser Pro Cys Glu Glu Arg Leu Asn Pro Ala Asp Ile Lys
        595                 600                 605

Arg Ala Ser Gln Leu Ala Ser Lys Met His Ser Leu Leu Ala Leu Met
610                 615                 620

Val Gly Leu Leu Thr Cys Gln Asp Ile Ile Asn Ser Asp Ala Glu His
625                 630                 635                 640

Phe Lys Glu Ser Glu Lys Val Ser Asp Ile Met Leu Gln Lys Leu Lys
                645                 650                 655

Ser Leu His Leu Lys Lys Lys Thr Leu Asp Lys Glu Leu Leu Lys His
            660                 665                 670

Lys Asp Arg Ile Thr Thr Phe Arg Glu Leu Ile Ala Lys Glu Lys Ala
        675                 680                 685

Phe Gln Asp His Ala Ile Lys Val Ile Asp Cys Asp Ser Asp Glu Ala
690                 695                 700

Lys Ser Ile Arg Asp Val Pro Thr Leu Leu Gly Ala Lys Leu Asp Lys
705                 710                 715                 720

Tyr His Ser Leu Asn Glu Glu Leu Asp Phe Leu Ile Thr Lys Leu Gly
                725                 730                 735

His Leu Leu Glu Ser Lys Glu Asn His Cys Asn Arg Leu Ile Glu Glu
            740                 745                 750
```

Asn Asp Lys Tyr Gln Arg His Leu Gly Asn Leu Ile Lys Val Thr
            755                 760                 765

Ser Tyr Glu Glu Ile Ile Glu Cys Ala Asp Gln Arg Leu Ala Ile Ser
    770                 775                 780

His Ser Gln Ile Ala His Leu Glu Glu Arg Asn Lys His Leu Glu Asp
785                 790                 795                 800

Leu Ile Arg Lys Pro Arg Glu Lys Ala Arg Lys Pro Arg Ser Lys Ser
                805                 810                 815

Leu Glu Asn His Pro Lys Ser Met Thr Met Met Pro Ala Leu Phe Lys
            820                 825                 830

Glu Asn Arg Asn Asp Leu Asp
            835

<210> SEQ ID NO 9
<211> LENGTH: 509
<212> TYPE: PRT
<213> ORGANISM: Homo sapiens

<400> SEQUENCE: 9

Met Glu Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
            115                 120                 125

His Gln Asp Phe Trp Thr Val Trp Ser Gly Asn Arg Ala Ser Leu Tyr
130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Asn Val Leu Arg Leu
                195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
                260                 265                 270

```
Ser Ser Tyr Ile Ser Pro Glu Lys Glu Glu Gln Tyr Ile Ala Gln Phe
            275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
                340                 345                 350

Val Leu Ser Leu Ser Gly Val Met Leu Thr Asp Val Ser Pro Glu Pro
            355                 360                 365

Leu Gln Ala Leu Leu Glu Arg Ala Ser Ala Thr Leu Gln Asp Leu Val
            370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
                420                 425                 430

Leu Ser Asn Leu Thr His Val Leu Tyr Pro Val Pro Leu Glu Ser Tyr
            435                 440                 445

Glu Asp Ile His Gly Thr Leu His Leu Glu Arg Leu Ala Tyr Leu His
            450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
                500                 505

<210> SEQ ID NO 10
<211> LENGTH: 9
<212> TYPE: PRT
<213> ORGANISM: Artificial Sequence
<220> FEATURE:
<223> OTHER INFORMATION: HLA binding peptide

<400> SEQUENCE: 10

Ile Leu Asn Asn Phe Pro His Ser Ile
1               5

<210> SEQ ID NO 11
<211> LENGTH: 9
<212> TYPE: PRT
<213> ORGANISM: Artificial Sequence
<220> FEATURE:
<223> OTHER INFORMATION: HLA binding peptide

<400> SEQUENCE: 11

Arg Ile Leu Val Asn Leu Ser Met Val
1               5

<210> SEQ ID NO 12
<211> LENGTH: 9
<212> TYPE: PRT
<213> ORGANISM: Artificial Sequence
<220> FEATURE:
<223> OTHER INFORMATION: HLA binding peptide
```

```
<400> SEQUENCE: 12

Val Leu Asp Gly Leu Asp Val Leu Leu
1               5

<210> SEQ ID NO 13
<211> LENGTH: 10
<212> TYPE: PRT
<213> ORGANISM: Artificial Sequence
<220> FEATURE:
<223> OTHER INFORMATION: HLA binding peptide

<400> SEQUENCE: 13

Ser Leu Tyr Ser Phe Pro Glu Pro Glu Ala
1               5                   10

<210> SEQ ID NO 14
<211> LENGTH: 10
<212> TYPE: PRT
<213> ORGANISM: Artificial Sequence
<220> FEATURE:
<223> OTHER INFORMATION: HLA binding peptide

<400> SEQUENCE: 14

Ala Leu Tyr Val Asp Ser Leu Phe Phe Leu
1               5                   10

<210> SEQ ID NO 15
<211> LENGTH: 9
<212> TYPE: PRT
<213> ORGANISM: Artificial Sequence
<220> FEATURE:
<223> OTHER INFORMATION: HLA binding peptide

<400> SEQUENCE: 15

Ser Leu Leu Gln His Leu Ile Gly Leu
1               5

<210> SEQ ID NO 16
<211> LENGTH: 9
<212> TYPE: PRT
<213> ORGANISM: Artificial Sequence
<220> FEATURE:
<223> OTHER INFORMATION: HLA binding peptide

<400> SEQUENCE: 16

Leu Pro Arg Glu Leu Phe Pro Pro Leu
1               5

<210> SEQ ID NO 17
<211> LENGTH: 10
<212> TYPE: PRT
<213> ORGANISM: Artificial Sequence
<220> FEATURE:
<223> OTHER INFORMATION: HLA binding peptide

<400> SEQUENCE: 17

Leu Pro Arg Arg Leu Phe Pro Pro Leu Phe
1               5                   10

<210> SEQ ID NO 18
<211> LENGTH: 9
<212> TYPE: PRT
<213> ORGANISM: Artificial Sequence
<220> FEATURE:
<223> OTHER INFORMATION: HLA binding peptide
```

```
<400> SEQUENCE: 18

Phe Pro Pro Leu Phe Met Ala Ala Phe
1               5

<210> SEQ ID NO 19
<211> LENGTH: 10
<212> TYPE: PRT
<213> ORGANISM: Artificial Sequence
<220> FEATURE:
<223> OTHER INFORMATION: HLA binding peptide

<400> SEQUENCE: 19

Ile Pro Val Glu Val Leu Val Asp Leu Phe
1               5                   10

<210> SEQ ID NO 20
<211> LENGTH: 10
<212> TYPE: PRT
<213> ORGANISM: Artificial Sequence
<220> FEATURE:
<223> OTHER INFORMATION: HLA binding peptide

<400> SEQUENCE: 20

Leu Pro Thr Leu Ala Lys Phe Ser Pro Tyr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: HLA binding peptide

<400> SEQUENCE: 21

Cys Pro His Cys Gly Asp Arg Thr Phe Tyr
1               5                   10

<210> SEQ ID NO 22
<211> LENGTH: 9
<212> TYPE: PRT
<213> ORGANISM: Artificial Sequence
<220> FEATURE:
<223> OTHER INFORMATION: HLA binding peptide

<400> SEQUENCE: 22

Glu Pro Ile Leu Cys Pro Cys Phe Met
1               5

<210> SEQ ID NO 23
<211> LENGTH: 9
<212> TYPE: PRT
<213> ORGANISM: Artificial Sequence
<220> FEATURE:
<223> OTHER INFORMATION: HLA binding peptide

<400> SEQUENCE: 23

Gly Gln His Leu His Leu Glu Thr Phe
1               5

<210> SEQ ID NO 24
<211> LENGTH: 9
<212> TYPE: PRT
<213> ORGANISM: Artificial Sequence
<220> FEATURE:
<223> OTHER INFORMATION: HLA binding peptide
```

```
<400> SEQUENCE: 24

Asn Leu Thr His Val Leu Tyr Pro Val
1               5

<210> SEQ ID NO 25
<211> LENGTH: 9
<212> TYPE: PRT
<213> ORGANISM: Artificial Sequence
<220> FEATURE:
<223> OTHER INFORMATION: HLA binding peptide

<400> SEQUENCE: 25

Lys Leu Val Glu Leu Glu His Thr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: HLA binding peptide

<400> SEQUENCE: 26

Tyr Leu Leu Leu Ala Ser Ser Ile Leu
1               5

<210> SEQ ID NO 27
<211> LENGTH: 9
<212> TYPE: PRT
<213> ORGANISM: Artificial Sequence
<220> FEATURE:
<223> OTHER INFORMATION: HLA binding peptide

<400> SEQUENCE: 27

Leu Leu Ala Ser Ser Ile Leu Cys Ala
1               5

<210> SEQ ID NO 28
<211> LENGTH: 9
<212> TYPE: PRT
<213> ORGANISM: Artificial Sequence
<220> FEATURE:
<223> OTHER INFORMATION: HLA binding peptide

<400> SEQUENCE: 28

Asn Leu Ser Met Val Glu Asn Lys Leu
1               5

<210> SEQ ID NO 29
<211> LENGTH: 783
<212> TYPE: DNA
<213> ORGANISM: Homo sapiens

<400> SEQUENCE: 29
aattgtgagg tctcgcgccc tcagccgtac ataaagcggg acaacacaga acttcccagt      60
tacaccaggc atcctggccc aaagtttccc aaatccaggc ggctagaggc ccactgcttc     120
ccaactacca gctgaggggg tccgtcccga aagggagaa gaggccgaag aggaaacatg     180
aacttctatt tactcctagc gagcagcatt ctgtgtgcct tgattgtctt ctggaaatat     240
cgccgctttc agagaaacac tggcgaaatg tcatcaaatt caactgctct tgcactagtg     300
agaccctctt cttctgggtt aattaacagc aatacagaca caatcttgc agtctacgac     360 ctctctcggg atattttaaa taatttccca cactcaatag ccaggcagaa gcgaatattg     420
```

-continued

| | |
|---|---|
| gtaaacctca gtatggtgga aaacaagctg gttgaactgg aacatactct acttagcaag | 480 |
| ggtttcagag gtgcatcacc tcaccggaaa tccacctaaa agcgtacagg atgtaatgcc | 540 |
| agtggtggaa atcattaaag acactttgag tagattcatt tgattgtgtg tttatactaa | 600 |
| atgaattatt tttttaagag ggaggggatt ccaagtcaca tacaaaaaat ccagatactt | 660 |
| accaagtttc ttatttatac tttaagtaat tgattacata tggctaaaat atacttactg | 720 |
| aggaaggaat ggaagcacaa tagagaaaga aaaacagttc aaaagtttgt taacaataaa | 780 |
| aaa | 783 |

<210> SEQ ID NO 30
<211> LENGTH: 22
<212> TYPE: DNA
<213> ORGANISM: Artificial Sequence
<220> FEATURE:
<223> OTHER INFORMATION: Oligonucleotide

<400> SEQUENCE: 30

| | |
|---|---|
| ccaaagtttc ccaaatccag gc | 22 |

<210> SEQ ID NO 31
<211> LENGTH: 29
<212> TYPE: DNA
<213> ORGANISM: Artificial Sequence
<220> FEATURE:
<223> OTHER INFORMATION: Oligonucleotide

<400> SEQUENCE: 31

| | |
|---|---|
| atctactcaa agtgtcttta atgatttcc | 29 |

<210> SEQ ID NO 32
<211> LENGTH: 22
<212> TYPE: DNA
<213> ORGANISM: Artificial Sequence
<220> FEATURE:
<223> OTHER INFORMATION: Oligonucleotide

<400> SEQUENCE: 32

| | |
|---|---|
| gtgtgccttg attgtcttct gg | 22 |

<210> SEQ ID NO 33
<211> LENGTH: 31
<212> TYPE: DNA
<213> ORGANISM: Artificial Sequence
<220> FEATURE:
<223> OTHER INFORMATION: Oligonucleotide

<400> SEQUENCE: 33

| | |
|---|---|
| gtatctggat tttttgtatg tgacttggaa t | 31 |

<210> SEQ ID NO 34
<211> LENGTH: 24
<212> TYPE: DNA
<213> ORGANISM: Artificial Sequence
<220> FEATURE:
<223> OTHER INFORMATION: Oligonucleotide

<400> SEQUENCE: 34

| | |
|---|---|
| ctttctctat tgtgcttcca ttcc | 24 |

<210> SEQ ID NO 35
<211> LENGTH: 19
<212> TYPE: DNA
<213> ORGANISM: Artificial Sequence

```
<220> FEATURE:
<223> OTHER INFORMATION: Oligonucleotide

<400> SEQUENCE: 35
cctggctatt gagtgtggg                                                  19

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide

<400> SEQUENCE: 36
gactcttcct ggagtggttg a                                               21

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
gaaccccgga agtggaggtt                                                 20

<210> SEQ ID NO 38
<211> LENGTH: 21
<212> TYPE: DNA
<213> ORGANISM: Artificial Sequence
<220> FEATURE:
<223> OTHER INFORMATION: Oligonucleotide

<400> SEQUENCE: 38
ggtcatggac ttcggatgat t                                               21

<210> SEQ ID NO 39
<211> LENGTH: 25
<212> TYPE: DNA
<213> ORGANISM: Artificial Sequence
<220> FEATURE:
<223> OTHER INFORMATION: Oligonucleotide

<400> SEQUENCE: 39
aggatttaat tagaaagccc agaga                                           25

<210> SEQ ID NO 40
<211> LENGTH: 22
<212> TYPE: DNA
<213> ORGANISM: Artificial Sequence
<220> FEATURE:
<223> OTHER INFORMATION: Oligonucleotide

<400> SEQUENCE: 40
ctctacccct gtatttcgct tg                                              22

<210> SEQ ID NO 41
<211> LENGTH: 476
<212> TYPE: DNA
<213> ORGANISM: Homo sapiens

<400> SEQUENCE: 41
ggatccctgt ggggccaggc aggaagggcc tgcttgggga cccagcgagc tcccagggcc     60
tttcccgctg cttcctctac ccctgtattt cgcttggctc tctaaattga ctcagctcca    120
```

```
gtttggaaga gagaaataaa catttagagg atttaattag aaagcccaga gaaaaagcca    180
gaaaaccaag atcaaaaagc ttagaaaatc atccgaagtc catgaccatg atgccagctc    240
tttttaaaga aaatagaaat gatttagatt aaacaagcct gaagattaaa cagtaatcat    300
ttttgtcaac cactccagga agagtcatta ctacatatgc tagccaaatc aatccatgca    360
gatgatatat taaaatctgt ataaagggta aagtcttaca ttccaaagat gtgattactt    420
ttcttctaat ttcttcctgt gaataatcaa atatattcta tttaacataa acagaa       476
```

```
<210> SEQ ID NO 42
<211> LENGTH: 603
<212> TYPE: DNA
<213> ORGANISM: Homo sapiens

<400> SEQUENCE: 42
ggatccctgt ggggccaggc aggaagggcc tgcttgggga cccagcgagc tcccagggcc     60
tttcccgctg cttcctctac ccctgtattt cgcttggctc tctaaattga ctcagctcca    120
gtttggaaga gagaaataaa catttagagg atttaattag aaagcccaga gaaaaagcca    180
gaaaaccaag atcaaaaagc ttagaaaatc atccgaagtc catgaccatg acggagtttc    240
actcttgttg cccaggctgg agtgcaatgg cgcaatctcg gctcactgca acctccactt    300
ccggggttca gtgattctc ctgcctcagc ctcccgagta gctggggtta caggcagatg     360
ccagctcttt ttaaagaaaa tagaaatgat ttagattaaa caagcctgaa gattaaacag    420
taatcatttt tgtcaaccac tccaggaaga gtcattacta catatgctag ccaaatcaat    480
ccatgcagat gatatattaa aatctgtata aagggtaaag tcttacattc caaagatgtg    540 attactttc ttctaatttc ttcctgtgaa taatcaaata tattctattt aacataaaca     600
gaa                                                                  603
```

```
<210> SEQ ID NO 43
<211> LENGTH: 53
<212> TYPE: PRT
<213> ORGANISM: Homo sapiens

<400> SEQUENCE: 43

Leu Ser Ser Ser Leu Glu Glu Arg Asn Lys His Leu Glu Asp Leu Ile
1               5                   10                  15

Arg Lys Pro Arg Glu Lys Ala Arg Lys Pro Arg Ser Lys Ser Leu Glu
            20                  25                  30

Asn His Pro Lys Ser Met Thr Met Pro Ala Leu Phe Lys Glu Asn
        35                  40                  45

Arg Asn Asp Leu Asp
    50
```

```
<210> SEQ ID NO 44
<211> LENGTH: 76
<212> TYPE: PRT
<213> ORGANISM: Homo sapiens

<400> SEQUENCE: 44

Leu Ser Ser Ser Leu Glu Glu Arg Asn Lys His Leu Glu Asp Leu Ile
1               5                   10                  15

Arg Lys Pro Arg Glu Lys Ala Arg Lys Pro Arg Ser Lys Ser Leu Glu
            20                  25                  30

Asn His Pro Lys Ser Met Thr Met Thr Glu Phe His Ser Cys Cys Pro
        35                  40                  45
```

```
Gly Trp Ser Ala Met Ala Gln Ser Arg Leu Thr Ala Thr Ser Thr Ser
    50                  55                  60

Gly Val Gln Val Ile Leu Leu Pro Gln Pro Pro Glu
65                  70                  75

<210> SEQ ID NO 45
<211> LENGTH: 121
<212> TYPE: DNA
<213> ORGANISM: Homo sapiens

<400> SEQUENCE: 45
ggatccctgt ggggccaggc aggaagggcc tgcttgggga cccagcgagc tcccagggcc         60
tttcccgctg cttcctctac ccctgtattt cgcttggctc tctaaattga ctcagctcca        120
g                                                                       121

<210> SEQ ID NO 46
<211> LENGTH: 127
<212> TYPE: DNA
<213> ORGANISM: Homo sapiens

<400> SEQUENCE: 46
acggagtttc actcttgttg cccaggctgg agtgcaatgg cgcaatctcg gctcactgca         60
acctccactt ccggggttca agtgattctc ctgcctcagc ctcccgagta gctgggtta        120 caggcag                                                                 127
```

TUMOR ANTIGENS FOR DETERMINING CANCER THERAPY

CROSS REFERENCE TO RELATED APPLICATION

The application is a National Phase Under 35 U.S.C. § 371 of International Application No. PCT/EP2014/066328 filed on Jul. 30, 2014, which claims the benefit of International Application Nos. PCT/EP2013/002271 filed on Jul. 30, 2013 and PCT/EP2013/003173 filed Oct. 22, 2013, the entire contents of which are herein incorporated by reference.

REFERENCE TO SEQUENCE LISTING

The Sequence Listing submitted Jan. 28, 2016 as a text file named "37592_0002U1_Sequence_Listing" created on Jan. 27, 2016, and having a size of 50,467 bytes is hereby incorporated by reference pursuant to 37 C.F.R. § 1.52(e)(5).

TECHNICAL FIELD OF THE INVENTION

The present invention relates to the treatment of cancer, in particular breast cancer, particularly triple-negative breast cancer. More particularly, the invention concerns methods and means for cancer treatment involving a specific set of tumor antigens.

BACKGROUND OF THE INVENTION

Breast cancer is a type of cancer originating from breast tissue, most commonly from the inner lining of milk ducts or the lobules that supply the ducts with milk. Occasionally, breast cancer presents as metastatic disease. Common sites of metastasis include bone, liver, lung and brain. Treatment of breast cancer may include surgery, medications (hormonal therapy and chemotherapy), radiation and/or immunotherapy.

Breast cancer cells may or may not have three important receptors: estrogen receptor (ER), progesterone receptor (PR), and HER2. ER positive and PR positive breast cancers can be treated with drugs that either block the receptors, e.g. tamoxifen (Nolvadex), or alternatively block the production of estrogen with an aromatase inhibitor, e.g. anastrozole (Arimidex) or letrozole (Femara). Aromatase inhibitors, however, are only suitable for post-menopausal patients. This is because the active aromatase in postmenopausal women is different from the prevalent form in premenopausal women, and therefore these agents are ineffective in inhibiting the predominant aromatase of premenopausal women.

Chemotherapy is predominately used for stage 2-4 disease and is particularly beneficial in ER negative disease. They are given in combinations, usually for 3-6 months. One of the most common treatments is cyclophosphamide plus doxorubicin (adriamycin), known as AC. Most chemotherapy medications work by destroying fast-growing and/or fast-replicating cancer cells either by causing DNA damage upon replication or other mechanisms; these drugs also damage fast-growing normal cells where they cause serious side effects. Damage to the heart muscle is the most dangerous complication of doxorubicin. Sometimes a taxane drug, such as docetaxel, is added, and the regime is then known as CAT; taxane attacks the microtubules in cancer cells. Another common treatment, which produces equivalent results, is cyclophosphamide, methotrexate, and fluorouracil (CMF).

Trastuzumab (Herceptin), a monoclonal antibody to HER2, is only effective in patients with HER2 amplification/overexpression. Trastuzumab, however, is expensive, and approximately 2% of patients suffer significant heart damage. Other monoclonal antibodies are also undergoing clinical trials. Between 25 and thirty percent of breast cancers have an amplification of the HER2 gene or overexpression of its protein product. Overexpression of this receptor in breast cancer is associated with increased disease recurrence and worse prognosis.

Antigen-specific immunotherapy aims to enhance or induce specific immune responses in patients and has been successfully used to control cancer diseases. In particular, T cells play a central role in cell-mediated immunity in humans and animals. The recognition and binding of a particular antigen is mediated by the T cell receptors (TCRs) expressed on the surface of T cells. The T cell receptor (TCR) of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell.

The present application relates to the identification of a set of tumor antigens (tumor antigen target portfolio) which is useful in a large fraction of cancer patients, in particular breast cancer patients, particularly triple-negative breast cancer patients. The tumor antigens of said tumor antigen target portfolio are shared tumor antigens which are expressed in a large fraction of cancer patients. The tumor antigen target portfolio identified according to the invention may be used for designing a drug repository for "off the shelf" pre-manufactured vaccines (warehouse). These vaccines are useful for treating a large fractions of cancer patients.

Specifically, the present invention may involve the identification of the patient-specific expression pattern of the tumor antigen target portfolio identified according to the invention and selecting a cancer therapy regimen based on said individual expression pattern, preferably by selecting suitable vaccines from pre-manufactured vaccines targeting expressed tumor antigens of the tumor antigen target portfolio. Alternatively, the present invention may involve the administration of pre-manufactured vaccines targeting the tumor antigen target portfolio identified according to the invention, preferably without prior identification of the patient-specific expression pattern of this tumor antigen target portfolio.

For vaccination, preferably epitopes from tumor antigens of the tumor antigen target portfolio identified according to the invention are provided to a patient for presentation by MHC molecules and stimulation of appropriate T cells. In one embodiment, said epitopes are provided as a part of a larger unit such as in the form of an entire tumor antigen or a portion thereof or in the form of a polypeptide comprising said epitopes and following appropriate processing and presentation by MHC molecules the epitopes are displayed to the patient's immune system for stimulation of appropriate T cells. The immunogenic products such as the tumor antigens or portions thereof or polypeptides comprising one or more immunogenic epitopes from one or more tumor antigens of the tumor antigen target portfolio against which an immune response is to be induced are preferably administered to a patient as RNA encoding the immunogenic products. In particular, in vitro transcribed RNA (IVT-RNA) may be directly injected into a patient by different immunization routes and following translation of the RNA in transfected cells the expression product following processing may be presented on MHC molecules on the surface of the cells to elicit an immune response. The advantages of using RNA as a kind of reversible gene therapy include transient expression and a non-transforming character. RNA does not need to enter the nucleus in order to be expressed and moreover cannot integrate into the host genome, thereby eliminating the risk of oncogenesis. Transfection rates attainable with RNA are relatively high. Furthermore, the amounts of protein achieved correspond to those in physiological expression.

DESCRIPTION OF INVENTION

Summary of the Invention

The present invention relates to methods for treating cancer, in particular breast cancer, particularly triple-negative breast cancer, involving a specific set of tumor antigens (tumor antigen target portfolio) expressed in a large fraction of patients. In particular, the present invention relates to methods for inducing an immune response in a cancer patient by administering cancer vaccines targeting a tumor antigen target portfolio or tumor antigens selected from a tumor antigen target portfolio. Preferably, the cancer vaccines administered according to the invention to a patient provide MHC presented epitopes which are suitable for stimulating, priming and/or expanding T cells directed against cells expressing antigens of said tumor antigen target portfolio from which the MHC presented epitopes are derived. Thus, the vaccines described herein are preferably capable of inducing or promoting a cellular response, preferably cytotoxic T cell activity, against a cancer disease characterized by presentation of one or more of said antigens with class I MHC.

According to the invention, a vaccine for inducing an immune response is preferably selected from a pre-furnished vaccine warehouse such as a pre-furnished RNA vaccine warehouse. This approach is also referred to as "off the shelf" herein. Such pre-furnished vaccine warehouse relates to a set comprising pre-manufactured vaccine products each pre-manufactured vaccine product inducing an immune response against a tumor antigen recited herein such as CXorf61, CAGE1 or PRAME. According to the invention, such warehouse is designed for being applicable to a large fraction of cancer patients. Since such vaccine warehouse is selected so as to be applicable to a large fraction of patients, it will be possible to select from said pre-furnished vaccine warehouse one or more vaccine products that will induce an immune response against one or more tumor antigens expressed in cancer cells of a particular patient being treated and, thus, targeting the tumor antigen profile of a respective patient without the need of providing further vaccine products specifically designed for the patient being treated. Such selection can be done by testing the patient for tumor antigen expression and then selecting appropriate vaccine products from the pre-furnished vaccine warehouse targeting said tumor antigens expressed by cancer cells of the patient. Such selection can be made based on the transcriptomic/peptidomic analysis of the patients tumor. For example, tumor samples from eligible patients can be analysed for their tumor antigen expression patterns. The tumor antigen expression pattern can be determined by quantitative, multiplex RT-PCR and IHC and the respective vaccine products can be selected from the warehouse. Selection from said pre-furnished vaccine warehouse of one or more vaccine products that will induce an immune response against one or more tumor antigens expressed in cancer cells of a particular patient being treated and, thus, targeting the tumor antigen profile of a respective patient can also be done by randomly selecting vaccine products from the pre-furnished vaccine warehouse which based on empirical data will most likely target one or more tumor antigens expressed by cancer cells of the patient. According to the invention the term "tumor antigen profile" refers to a collection of tumor antigens expressed in cancer cells of a patient.

A vaccine for inducing an immune response, when administered to a patent, preferably provides MHC presented epitopes from one or more of the tumor antigens mentioned herein. Presentation of these epitopes by cells of a patient, in particular antigen presenting cells, preferably results in T cells targeting the epitopes when bound to MHC and thus, the patient's tumor, preferably the primary tumor as well as tumor metastases, expressing antigens from which the MHC presented epitopes are derived and presenting the same epitopes on the surface of the tumor cells.

Administration of a vaccine according to the invention may provide MHC class II-presented epitopes that are capable of eliciting a CD4+ helper T cell response against cells expressing antigens from which the MHC presented epitopes are derived. Alternatively or additionally, administration of a vaccine according to the invention may provide MHC class I-presented epitopes that are capable of eliciting a CD8+ T cell response against cells expressing antigens from which the MHC presented epitopes are derived. Furthermore, administration of a vaccine according to the invention may provide one or more neo-epitopes as well as one or more epitopes not containing cancer specific somatic mutations. In one embodiment, administration of a vaccine according to the invention provides neo-epitopes that are MHC class II-presented epitopes and/or are capable of eliciting a CD4+ helper T cell response against cells expressing antigens from which the MHC presented epitopes are derived as well as epitopes not containing cancer-specific somatic mutations that are MHC class I-presented epitopes and/or are capable of eliciting a CD8+ T cell response against cells expressing antigens from which the MHC presented epitopes are derived.

According to the invention, epitopes of tumor antigens of the set of tumor antigens identified according to the invention may be present in a vaccine as polyepitopic polypeptide or nucleic acid such as RNA encoding such polyepitopic polypeptide. If it is intended to use a pre-manufactured polyepitopic polypeptide for inducing an immune response, the polyepitopic polypeptide is preferably administered without determining the patient's individual tumor antigen expression pattern. The polyepitopic polypeptide comprises epitopes which based on empirical data will most likely induce an immune response targeting one or more tumor antigens expressed by cancer cells of the patient. To this end, it is demonstrated in the examples that a specific set of only three different tumor antigens is sufficient so as to cover 95% of the triple-negative breast cancer (TNBC) patient samples analyzed. In other words, 95% of the TNBC patients express at least one antigen which is among said specific set of only three different tumor antigens. Thus, including into a polyepitopic polypeptide at least one epitope from each of said three different tumor antigens would be expected to induce an immune response in 95% of the TNBC patients.

One aspect of the invention relates to a method for treating cancer in a patient comprising determining the expression pattern of a set of tumor antigens and selecting a cancer therapy regimen based on the expression pattern determined, wherein the set of tumor antigens comprises CXorf61 and CAGE1. In one embodiment, the set of tumor antigens further comprises PRAME. In another embodiment, the set of tumor antigens further comprises one or more antigens selected from the group consisting of CBX2, PLAC1, CLDN6, SPANX, MAGEA3, TPTE, ACTL8, ANKRD30A, CDKN2A, MAD2L1, CTAG1B, MAGEA4, MAGEA5, SUNC1, MAGEA10, LRRN1 and MAGEA9.

In one embodiment, the expression pattern is determined in a sample obtained from a cancer patient. In one embodiment, the sample comprises cancer cells. In one embodiment, the sample is a tumor specimen of the cancer patient.

In one embodiment, determining the expression pattern comprises a quantitative and/or qualitative determination of the expression of the tumor antigens. In one embodiment, determining the expression pattern comprises determining the expression of RNA and/or protein of the tumor antigens.

In one embodiment, the cancer therapy regimen based on the expression pattern determined comprises immunotherapeutically targeting those tumor antigens of the set of tumor antigens which are expressed in cancer cells of the patient. In one embodiment, the cancer therapy regimen based on the expression pattern determined comprises inducing an immune response in the patient against those tumor antigens of the set of tumor antigens which are expressed in cancer cells of the patient. In one embodiment, the immune response is induced by providing to the patient one or more immunogenic epitopes of each of those tumor antigens of the set of tumor antigens which are expressed in cancer cells of the patient.

In one embodiment, the immune response comprises a cellular response. In one embodiment, the immune response comprises a CD8+ T cell response and/or a CD4+ T cell response. In one embodiment, the cellular response is induced by administering to the patient a vaccine providing one or more T cell epitopes of each of those tumor antigens of the set of tumor antigens which are expressed in cancer cells of the patient. In one embodiment, the one or more T cell epitopes are comprised in the vaccine in one or more peptides or polypeptides wherein said one or more peptides or polypeptides following administration are processed to produce the one or more T cell epitopes. In one embodiment, the vaccine is an RNA vaccine. In one embodiment, following appropriate processing and presentation by MHC molecules the T cell epitopes are displayed to the patient's immune system for stimulation of appropriate T cells.

A further aspect of the invention relates to a method for preventing or treating cancer in a patient comprising immunotherapeutically targeting each tumor antigen of a set of tumor antigens, wherein the set of tumor antigens comprises CXorf61 and CAGE1. In one embodiment, the set of tumor antigens further comprises PRAME. In another embodiment, the set of tumor antigens further comprises one or more antigens selected from the group consisting of CBX2, PLAC1, CLDN6, SPANX, MAGEA3, TPTE, ACTL8, ANKRD30A, CDKN2A, MAD2L1, CTAG1B, MAGEA4, MAGEA5, SUNC1, MAGEA10, LRRN1 and MAGEA9.

In one embodiment, the method of the invention comprises inducing an immune response in the patient against each tumor antigen of the set of tumor antigens. In one embodiment, the immune response is induced by providing to the patient one or more immunogenic epitopes of each tumor antigen of the set of tumor antigens.

In one embodiment, the immune response comprises a cellular response. In one embodiment, the immune response comprises a CD8+ T cell response and/or a CD4+ T cell response. In one embodiment, the cellular response is induced by administering a vaccine providing one or more T cell epitopes of each tumor antigen of the set of tumor antigens to the patient. In one embodiment, the one or more T cell epitopes are comprised in the vaccine in one or more peptides or polypeptides wherein said one or more peptides or polypeptides following administration are processed to produce the one or more T cell epitopes. In one embodiment, the vaccine is an RNA vaccine. In one embodiment, following appropriate processing and presentation by MHC molecules the T cell epitopes are displayed to the patient's immune system for stimulation of appropriate T cells.

In one embodiment of all aspects of the invention, the cancer is breast cancer. In one embodiment of all aspects of the invention, the cancer is triple-negative breast cancer.

A further aspect of the invention relates to a set of vaccine products comprising vaccine products for inducing an immune response against each tumor antigen of a set of tumor antigens in a patient, wherein the set of tumor antigens comprises CXorf61 and CAGE1. In one embodiment, the set of tumor antigens further comprises PRAME. In another embodiment, the set of tumor antigens further comprises one or more antigens selected from the group consisting of CBX2, PLAC1, CLDN6, SPANX, MAGEA3, TPTE, ACTL8, ANKRD30A, CDKN2A, MAD2L1, CTAG1B, MAGEA4, MAGEA5, SUNC1, MAGEA10, LRRN1 and MAGEA9.

In one embodiment, the vaccine products when administered to a patient provide one or more immunogenic epitopes of each tumor antigen of the set of tumor antigens.

In one embodiment, the immune response comprises a cellular response. In one embodiment, the immune response comprises a CD8+ T cell response and/or a CD4+ T cell response. In one embodiment, the vaccine products when administered to a patient provide one or more T cell epitopes of each tumor antigen of the set of tumor antigens. In one embodiment, the set of vaccine products of the invention comprises one or more peptides or polypeptides comprising the one or more T cell epitopes. In one embodiment, following appropriate processing and presentation by MHC molecules the T cell epitopes are displayed to the patients immune system for stimulation of appropriate T cells. In one embodiment, the vaccine products are RNA vaccines.

A further aspect of the invention relates to a kit for determining the expression pattern of a set of tumor antigens, wherein the set of tumor antigens comprises CXorf61 and CAGE1 and wherein the kit comprises reagents specifically binding to each tumor antigen of said set of tumor antigens or nucleic acids coding therefor. In one embodiment, the set of tumor antigens further comprises PRAME and the set of reagents further comprises reagents specifically binding to PRAME or a nucleic acid coding therefor. In another embodiment, the set of tumor antigens further comprises one or more antigens selected from the group consisting of CBX2, PLAC1, CLDN6, SPANX, MAGEA3, TPTE, ACTL8, ANKRD30A, CDKN2A, MAD2L1, CTAG1B, MAGEA4, MAGEA5, SUNC1, MAGEA10, LRRN1 and MAGEA9 and the set of reagents further comprises reagents specifically binding to said tumor antigens or nucleic acid coding therefor.

In one embodiment, the immunogenic epitopes used according to the invention may have patient-specific amino acid sequence modifications which may be based on cancer specific somatic mutations present in cancer cells of the patient. Thus, the present invention may involve: (a) identifying cancer specific somatic mutations in a tumor specimen of a cancer patient; and (b) using for immunization immunogenic epitopes or nucleic acids encoding said epitopes incorporating sequence modifications resulting from cancer specific somatic mutations determined in step (a).

Thus, a vaccine for inducing an immune response, when administered to a patent, may provide epitopes incorporating sequence changes based on the identified mutations or sequence differences. Such MHC presented epitopes incorporating sequence changes based on the identified mutations or sequence differences are also termed "neo-epitopes" herein.

The vaccines described herein may comprise a pharmaceutically acceptable carrier and may optionally comprise one or more adjuvants, stabilizers etc. The vaccines may in the form of a therapeutic or prophylactic vaccine.

In further aspects, the invention provides the vaccines described herein for use in the methods of treatment described herein, in particular for use in treating or preventing cancer.

The treatments of cancer described herein can be combined with surgical resection and/or radiation and/or traditional chemotherapy.

A further aspect of the invention relates to a method for determining the expression of the tumor antigen CXorf61 comprising the step of assaying a sample with respect to expression of a nucleic acid which comprises the nucleic acid sequence of SEQ ID NO: 29 or a variant of said nucleic acid sequence. Accordingly, if according to the invention the expression (pattern) of CXorf61 or a set of tumor antigens comprising CXorf61 is to be determined, said determination may comprise the step of assaying a sample with respect to expression of a nucleic acid which comprises the nucleic acid sequence of SEQ ID NO: 29 or a variant of the nucleic acid sequence.

A further aspect of the invention relates to a method for diagnosis, detection or monitoring, i.e. determining the regression, progression, course and/or onset, of cancer comprising the step of assaying a sample with respect to expression of a nucleic acid which comprises the nucleic acid sequence of SEQ ID NO: 29 or a variant of said nucleic acid sequence.

In the above aspects, assaying a sample with respect to expression of a nucleic acid may comprise a quantitative and/or qualitative determination of the expression of the nucleic acid.

Accordingly, the present invention relates to a method for diagnosis, detection or monitoring of cancer comprising the detection of and/or determination of the quantity of a nucleic acid which comprises the nucleic acid sequence of SEQ ID NO: 29 or a variant of said nucleic acid sequence, in a sample isolated from a patient, preferably from a patient having cancer, being suspected of having or falling ill with cancer or having a potential for cancer.

Preferably, the above methods involve the use of ligands such as nucleic acid probes which specifically bind to the nucleic acid which is to be detected or the quantity of which is to be determined. The above methods may be used to detect whether a subject has or is at (increased) risk of developing cancer, or, for instance, whether a treatment regimen is efficient.

Preferably, the cancer which is to be diagnosed, detected or monitored using the methods of the invention is selected from the group consisting of ovarian cancer, lung cancer, gastric cancer, breast cancer, hepatic cancer, pancreatic cancer, esophageal cancer and prostate cancer. In a particularly preferred embodiment, the cancer is breast cancer, in particular triple-negative breast cancer.

Preferably, the cancer which is to be diagnosed, detected or monitored using the methods of the invention is a cancer disease wherein cancer cells express the tumor antigen CXorf61, more preferably wherein cancer cells express or aberrantly express the tumor antigen CXorf61 while cells of the non-cancerous tissue preferably do not express the tumor antigen CXorf61 or express the tumor antigen CXorf61 at a lower level.

Typically, the level of the target nucleic acid (i.e. the nucleic acid which is to be assayed or detected or the quantity of which is to be determined in the methods of the invention) in a sample is compared to a reference level. Preferably, a deviation from said reference level is indicative of the presence and/or stage of cancer in a subject. The reference level may be a level determined in one or more reference samples (e.g., samples from healthy tissues or subjects) or a median level from healthy tissues or subjects. Preferably, a test sample and (a) reference sample(s) are derived from the same tissue type and/or the reference level is a level determined in the same tissue type as the tissue to be tested (from which the test sample is derived). Preferably, a test sample is derived from a tissue which is to be diagnosed, detected or monitored with respect to cancer; e.g. the cancer which is to be diagnosed, detected or monitored is breast cancer and the sample and optionally reference sample(s) are derived from breast tissue. Preferably, the presence of the target nucleic acid in the sample or a quantity of the target nucleic acid in the sample which is increased compared to a reference level, e.g. compared to a patient without cancer, indicates the presence of or risk for (i.e. a potential for a development of) cancer.

In one embodiment, a sample in the above methods comprises cancer cells. In one embodiment, the sample is a tumor specimen of a cancer patient.

In one embodiment of the methods of the invention the sample is from a tissue or organ wherein the cells when the tissue or organ is free of cancer do not substantially express CXorf61.

In one embodiment, the sample is from a tissue or organ wherein the cells when the tissue or organ is free of cancer do not substantially express CXorf61 and the tissue or organ optionally has already been diagnosed as being affected by cancer, e.g. by visual inspection or culture testing of cells of said tissue or organ. In this embodiment, the presence of the target nucleic acid and/or a quantity of the target nucleic acid which is increased compared to a reference level, e.g. compared to a patient without cancer, may indicate that the cancer can be treated by immunotherapeutically targeting CXorf61 using, for example, the methods and means described herein.

The above methods preferably allow quantitative and/or qualitative evaluations, e.g., absolute and/or relative measurements of target nucleic acid.

If reference is made herein to the detection of or the determination of the quantity of a nucleic acid, the nucleic acid which is actually to be detected or the quantity of which is actually to be determined is preferably mRNA. However, it should be understood that this may also include embodiments wherein mRNA is detected or the quantity of mRNA is determined indirectly. For example, mRNA may be transformed into cDNA and the cDNA is detected or its quantity determined. mRNA is given herein as the cDNA equivalent. One skilled in the art would understand that the cDNA sequence is equivalent to the mRNA sequence, and can be used for the same purpose herein, e.g., the generation of probes hybridizing to the nucleic acid to be detected. Thus, if reference is made herein to the sequences shown in the sequence listing this is also to include the RNA equivalents of said sequences.

Means for detection and/or determination of the quantity of target nucleic acid are described herein and will be apparent to the skilled person.

Preferably, the detection and/or determination of the quantity of target nucleic acid comprises (i) contacting a sample with an agent which binds specifically to the target nucleic acid, and (ii) detecting the formation of and/or determining the quantity of a complex between the agent and the target nucleic acid.

Typically, the detection and/or determination of the quantity of the target nucleic acid involves the use of labeled ligands which specifically bind to the target nucleic acid, e.g. a labeled nucleic acid probe that hybridizes to the target nucleic acid.

According to the invention, detection of a nucleic acid or determining the quantity of a nucleic acid may be carried out using known nucleic acid detection methods such as methods involving hybridization or nucleic acid amplification techniques. In one embodiment, mRNA transcripts are detected or the quantity thereof is determined using RT-PCR or Northern blot analysis.

Such nucleic acid detection methods may involve the use of oligonucleotides hybridizing to the target nucleic acid. Suitable oligonucleotides typically vary in length from five to several hundred nucleotides, more typically about 20-70 nucleotides in length or shorter, even more typically about 10-30 nucleotides in length.

The methods of monitoring according to the invention preferably comprise a detection of and/or determination of the quantity of the target nucleic acid in a first sample at a first point in time and in a further sample at a second point in time, wherein a regression, progression, course and/or onset of cancer may be determined by comparing the two samples.

A quantity of the target nucleic acid which is decreased in a sample compared to a sample taken earlier from a patient may indicate a regression, a positive course, e.g. a successful treatment, or a reduced risk for an onset of cancer in said patient.

A quantity of the target nucleic acid which is increased in a sample compared to a sample taken earlier from a patient may indicate a progression, a negative course, e.g. an unsuccessful treatment, recurrence or metastatic behavior, an onset or a risk for an onset of cancer in said patient.

A further aspect of the invention relates to a kit useful in the above methods. These kits in one embodiment comprise a ligand that specifically binds to the target nucleic acid; i.e. a nucleic acid which comprises the nucleic acid sequence of SEQ ID NO: 29 or a variant of said nucleic acid sequence. In a particular embodiment, the ligand comprises nucleic acid primers or probes specific for the target nucleic acid as described above. Kits may include informative pamphlets, for example, pamphlets informing how to use reagents to practice a method disclosed herein.

In a further aspect, the invention relates to a nucleic acid molecule such as a recombinant nucleic acid molecule, in particular DNA or RNA molecule, which comprises the nucleic acid sequence of SEQ ID NO: 29 or a variant of said nucleic acid sequence.

The invention also relates to host cells which comprise the nucleic acid molecule of the invention. Preferably, such host cells express the protein encoded by the nucleic acid molecule. In one embodiment, the host cell is an antigen-presenting cell, in particular a dendritic cell, a monocyte or a macrophage.

The above aspects and disclosure with respect to CXorf61 and the nucleic acid sequence of SEQ ID NO: 29 analogously also apply to CAGE1 wherein the nucleic acid sequence of SEQ ID NOs: 41 or 42 or a variant of said nucleic acid sequences are concerned. For example, a further aspect of the invention relates to a method for determining the expression of the tumor antigen CAGE1 comprising the step of assaying a sample with respect to expression of a nucleic acid which comprises the nucleic acid sequence of SEQ ID NO: 41 or 42 or a variant of said nucleic acid sequences.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) *Helvetica Chimica Acta*, CH-4010 Basel, Switzerland.

The practice of the present invention will employ, unless otherwise indicated, conventional methods of biochemistry, cell biology, immunology, and recombinant DNA techniques which are explained in the literature in the field (cf, e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

According to the present invention, the term "peptide" refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "polypeptide" or "protein" refers to large peptides, preferably to peptides with more than 100 amino acid residues, but in general the terms "peptide", "polypeptide" and "protein" are synonyms and are used interchangeably herein.

According to the invention, the term "modification" with respect to peptides, polypeptides or proteins relates to a sequence change in a peptide, polypeptide or protein compared to a parental sequence such as the sequence of a wildtype peptide, polypeptide or protein. The term includes amino acid insertion variants, amino acid addition variants, amino acid deletion variants and amino acid substitution variants, preferably amino acid substitution variants. All these sequence changes may potentially create new epitopes.

Amino acid insertion variants comprise insertions of single or two or more amino acids in a particular amino acid sequence.

Amino acid addition variants comprise amino- and/or carboxy-terminal fusions of one or more amino acids, such as 1, 2, 3, 4 or 5, or more amino acids.

Amino acid deletion variants are characterized by the removal of one or more amino acids from the sequence, such as by removal of 1, 2, 3, 4 or 5, or more amino acids.

Amino acid substitution variants are characterized by at least one residue in the sequence being removed and another residue being inserted in its place.

The term "derived" means according to the invention that a particular entity, in particular a particular peptide sequence, is present in the object from which it is derived. In the case of amino acid sequences, especially particular sequence regions, "derived" in particular means that the relevant amino acid sequence is derived from an amino acid sequence in which it is present.

The term "immune response" refers to an integrated bodily response to a target such as an antigen or a cell expressing an antigen and preferably refers to a cellular immune response or a cellular as well as a humoral immune response. The immune response may be protective/preventive/prophylactic and/or therapeutic.

"Inducing an immune response" may mean that there was no immune response before induction, but it may also mean that there was a certain level of immune response before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor antigen may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

According to the invention, "inducing an immune response against" in connection with particular tumor antigens such as CXorf61, CAGE1 and/or PRAME preferably relates to the ability of inducing an immune response, preferably a T cell response against said tumor antigens or cells such as cancer cells expressing and/or presenting said tumor antigens in a patient. Thus, a vaccine for inducing an immune response against a tumor antigen may comprise a peptide or polypeptide comprising one or more immunogenic epitopes of the tumor antigen such as a polypeptide comprising the tumor antigen or a portion thereof, in particular a portion comprising an immunogenic epitope of the tumor antigen. In one particularly preferred embodiment, such peptide or polypeptide according to the present invention is administered to a patient in the form of a nucleic acid, preferably RNA such as in vitro transcribed or synthetic RNA, which may be expressed in cells of a patient such as antigen presenting cells to produce the peptide or polypeptide.

The terms "cellular immune response" and "cellular response" or similar terms refer to an immune response directed to cells characterized by presentation of an antigen with class I or class II MHC involving T cells or T-lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill diseased cells such as cancer cells, preventing the production of more diseased cells. In preferred embodiments, the present invention involves the stimulation of an anti-tumor CTL response against tumor cells expressing one or more tumor antigens and preferably presenting such tumor antigens with class I MHC.

An "antigen" according to the invention covers any substance, preferably a peptide or protein, that is a target of and/or induces an immune response such as a specific reaction with antibodies or T-lymphocytes (T cells). Preferably, an antigen comprises at least one epitope such as a T cell epitope. Preferably, an antigen in the context of the present invention is a molecule which, optionally after processing, induces an immune reaction, which is preferably specific for the antigen (including cells expressing the antigen). The antigen or a T cell epitope thereof is preferably presented by a cell, preferably by an antigen presenting cell which includes a diseased cell, in particular a cancer cell, in the context of MHC molecules, which results in an immune response against the antigen (including cells expressing the antigen).

In one embodiment, an antigen is a tumor antigen (also termed tumor-expressed antigen herein), i.e., a part of a tumor cell such as a protein or peptide expressed in a tumor cell which may be derived from the cytoplasm, the cell surface or the cell nucleus, in particular those which primarily occur intracellularly or as surface antigens of tumor cells. For example, tumor antigens include CXorf61, CAGE1 and PRAME. According to the present invention, a tumor antigen preferably comprises any antigen which is expressed in and optionally characteristic with respect to type and/or expression level for tumors or cancers as well as for tumor or cancer cells, i.e. a tumor-associated antigen. In one embodiment, the term "tumor-associated antigen" relates to proteins that are under normal conditions specifically expressed in a limited number of tissues and/or organs or in specific developmental stages, for example, the tumor-associated antigens may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system.

According to the invention, the terms "tumor antigen", "tumor-expressed antigen", "cancer antigen" and "cancer-expressed antigen" are equivalents and are used interchangeably herein.

The term "CXorf61" relates to a protein comprising, preferably consisting of the amino acid sequence of SEQ ID NO: 3 of the sequence listing or a variant of said amino acid sequence and to a gene that encodes the protein. According to the invention, peptides comprising, preferably consisting of the amino acid sequence of SEQ ID NO: 10 or 11 of the sequence listing or variants of said amino acid sequences are useful as T cell epitopes for eliciting an immune response against cells expressing CXorf61.

The term "CAGE1" relates to a protein comprising, preferably consisting of the amino acid sequence of SEQ ID NO: 4, 5, 6, 7, 8, 43 or 44, preferably SEQ ID NO: 4, 5, 6, 7 or 8 of the sequence listing or a variant of said amino acid sequence and to a gene that encodes the protein.

The term "PRAME" relates to a protein comprising, preferably consisting of the amino acid sequence of SEQ ID NO: 9 of the sequence listing or a variant of said amino acid sequence and to a gene that encodes the protein. According to the invention, peptides comprising, preferably consisting of the amino acid sequence of SEQ ID NO: 12, 13, 14, 15, 16, 17, 18, 19, 20, 21, 22, 23 or 24 of the sequence listing or variants of said amino acid sequences are useful as T cell epitopes for eliciting an immune response against cells expressing PRAME.

According to the invention, the term "neoantigen" relates to an antigen including one or more amino acid modifications compared to the parental antigen. For example, a neoantigen may be a tumor-associated neoantigen, wherein the term "tumor-associated neoantigen" includes a peptide or protein including amino acid modifications due to tumor-specific mutations.

According to the invention, the term "tumor-specific mutation" or "cancer-specific mutation" relates to a somatic mutation that is present in the nucleic acid of a tumor or cancer cell but absent in the nucleic acid of a corresponding normal, i.e. non-tumorous or non-cancerous, cell. The terms "tumor-specific mutation" and "tumor mutation" and the terms "cancer-specific mutation" and "cancer mutation" are used interchangeably herein.

According to the invention, the term "tumor antigen-positive cancer" or "tumor antigen-positive tumor" or similar terms means a cancer or tumor involving cancer or tumor cells expressing a tumor antigen.

The term "immunogenicity" relates to the relative effectively to induce an immune response that is preferably associated with therapeutic treatments, such as treatments against cancers. As used herein, the term "immunogenic" relates to the property of having immunogenicity. For example, the term "immunogenic" when used in the context of a peptide, polypeptide or protein relates to the effectively of said peptide, polypeptide or protein to induce an immune response that is caused by and/or directed against said peptide, polypeptide or protein.

According to the invention, the immunotherapeutic targeting of an antigen such as a tumor antigen can be effected by any means which result in an immune response or immune reaction targeting said antigen, including cells expressing said antigen and optionally presenting the antigen in the context of MHC molecules. Such immunotherapeutic targeting provides for the selective eradication of cells that express the antigen and optionally present said antigen, thereby minimizing adverse effects to normal cells not expressing and optionally not presenting said antigen.

According to the invention, the term "immunotherapeutic targeting", in particular, relates to any therapy involving the immune system, components thereof or immune mechanisms that can be used to target preferentially diseased cells such as cells expressing tumor antigen(s) and optionally presenting tumor antigen(s) such as cancer cells while non-diseased cells not expressing tumor antigen(s) are not targeted or targeted to a lesser extent. Targeting of diseased cells preferably results in killing and/or impairment of proliferation or viability of diseased cells.

According to the invention active and/or passive immunotherapeutic strategies are envisioned for immunotherapeutic targeting. Active immunotherapeutic strategies may aim to induce, i.e. activate or sensitize, and expand antigen-specific T cells in the patient, which are able to specifically recognize and kill diseased cells. Different antigen formats can be used for tumor vaccination including proteins, peptides or nucleic acids such as RNA that can be applied either directly in vivo or in vitro by pulsing of DCs following transfer into the patient. Passive immunotherapeutic strategies rely, for example, on the adoptive transfer of immunoreactive cells, such as lymphoid cells, in particular T cells. T cells may optionally be engineered in vitro to express a defined antigen-specific T cell receptor (TCR) specifically targeting a tumor antigen (presented in the context of MHC molecules). Nucleic acids such as RNA encoding T cell receptor (TCR) chains may be introduced into T cells. In a suitable embodiment, the TCR α- and β-chains are cloned out from an antigen-specific T cell line and used for adoptive T cell therapy. The T cell receptors are preferably specific for an antigen which includes specificity for a peptide fragment derived from the antigen and presented in the context of MHC molecules. In general, the T cell receptors recognize or bind antigen peptides presented in the context of MHC. The nucleic acids encoding α- and β-chains of a T cell receptor may be contained on separate nucleic acid molecules such as expression vectors or alternatively, on a single nucleic acid molecule. Accordingly, the term "a nucleic acid encoding a T cell receptor" relates to nucleic acid molecules encoding the T cell receptor chains on the same or preferably on different nucleic acid molecules. According to the invention, T cells may be stimulated, primed and/or expanded in vitro or in vivo. The T cells used for treatment according to the invention may be autologous, allogeneic or syngeneic to a treated subject.

Adoptive cell transfer (ACT) based immunotherapy can be broadly defined as a form of passive immunization with previously sensitized cells, in particular T cells, that are transferred to recipients or to the autologous host after ex vivo expansion from low precursor frequencies to clinically relevant cell numbers. Since the antigenic specificity of T cells is rested entirely on the heterodimeric complex of the TCR α- and β-chain, the transfer of cloned TCR genes into T cells offers the potential to redirect them towards any antigen of interest. Therefore, TCR gene therapy provides an attractive strategy to develop antigen-specific immunotherapy with autologous lymphocytes as treatment option.

Other forms of immunotherapeutic strategies may involve targeting of disease-associated antigen(s) such as cell surface antigen(s) on diseased cells by antibodies, antibody fragments, or antibody derivatives that are either naked or conjugated to a therapeutic moiety such as cytotoxins or radionuclides. Antibodies, antibody fragments, or antibody derivatives that are not conjugated to a therapeutic moiety may act through recruiting the patient's immune system to destroy tumor cells, e.g. by inducing complement dependent cytotoxicity (CDC) and/or antibody-dependent cell-mediated cytotoxicity (ADCC).

Strategies involving antibodies may be applied as active and/or passive immunotherapeutic strategies.

The terms "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and non-self antigens (e.g., fragments of invading microorganisms) to a T cell.

The MHC region is divided into three subgroups, class I, class II, and class III. MHC class I proteins contain an α-chain and β2-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells, MHC class III region encodes for other immune components, such as complement components and some that encode cytokines. The MHC is both polygenic (there are several MHC class I and MHC class II genes) and polymorphic (there are multiple alleles of each gene).

As used herein, the term "haplotype" refers to the HLA alleles found on one chromosome and the proteins encoded thereby. Haplotype may also refer to the allele present at any one locus within the MHC. Each class of MHC is represented by several loci: e.g., HLA-A (Human Leukocyte Antigen-A), HLA-B, HLA-C, HLA-E, HLA-F, HLA-G, HLA-H, HLA-J, HLA-K, HLA-L, HLA-P and HLA-V for class I and HLA-DRA, HLA-DRB1-9, HLA-, HLA-DQA1, HLA-DQB1, HLA-DPA1, HLA-DPB1, HLA-DMA, HLA-DMB, HLA-DOA, and HLA-DOB for class II. The terms "HLA allele" and "MHC allele" are used interchangeably herein.

The MHCs exhibit extreme polymorphism: within the human population there are, at each genetic locus, a great number of haplotypes comprising distinct alleles. Different polymorphic MHC alleles, of both class I and class II, have different peptide specificities: each allele encodes proteins that bind peptides exhibiting particular sequence patterns.

In one preferred embodiment of all aspects of the invention an MHC molecule is an HLA molecule.

In the context of the present invention, the term "MHC binding peptide" includes MHC class I and/or class II binding peptides or peptides that can be processed to produce MHC class I and/or class II binding peptides. In the case of class I MHC/peptide complexes, the binding peptides are typically 8-12, preferably 8-10 amino acids long although longer or shorter peptides may be effective. In the case of class II MHC/peptide complexes, the binding peptides are typically 9-30, preferably 10-25 amino acids long and are in particular 13-18 amino acids long, whereas longer and shorter peptides may be effective.

If a peptide is to be presented directly, i.e., without processing, in particular without cleavage, it has a length which is suitable for binding to an MHC molecule, in particular a class I MHC molecule, and preferably is 7-30 amino acids in length such as 7-20 amino acids in length, more preferably 7-12 amino acids in length, more preferably 8-11 amino acids in length, in particular 9 or 10 amino acids in length.

If a peptide is part of a larger entity comprising additional sequences, e.g. of a vaccine sequence or polypeptide, and is to be presented following processing, in particular following cleavage, the peptide produced by processing has a length which is suitable for binding to an MHC molecule, in particular a class I MHC molecule, and preferably is 7-30 amino acids in length such as 7-20 amino acids in length, more preferably 7-12 amino acids in length, more preferably 8-11 amino acids in length, in particular 9 or 10 amino acids in length. Preferably, the sequence of the peptide which is to be presented following processing is derived from the amino acid sequence of an antigen or polypeptide used for vaccination, i.e., its sequence substantially corresponds and is preferably completely identical to a fragment of the antigen or polypeptide.

Thus, an MHC binding peptide in one embodiment comprises a sequence which substantially corresponds and is preferably completely identical to a fragment of an antigen.

The term "epitope" refers to an antigenic determinant in a molecule such as an antigen, i.e., to a part in or fragment of the molecule that is recognized by the immune system, for example, that is recognized by a T cell, in particular when presented in the context of MHC molecules. An epitope of a protein such as a tumor antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is particularly preferred that the epitope in the context of the present invention is a T cell epitope.

According to the invention an epitope may bind to MHC molecules such as MHC molecules on the surface of a cell and thus, may be a "MHC binding peptide".

As used herein the term "neo-epitope" refers to an epitope that is not present in a reference such as a normal non-cancerous or germline cell but is found in cancer cells. This includes, in particular, situations wherein in a normal non-cancerous or germline cell a corresponding epitope is found, however, due to one or more mutations in a cancer cell the sequence of the epitope is changed so as to result in the neo-epitope.

As used herein, the term "T cell epitope" refers to a peptide which binds to a MHC molecule in a configuration recognized by a T cell receptor. Typically, T cell epitopes are presented on the surface of an antigen-presenting cell.

According to the invention, a T cell epitope may be present in a vaccine as a part of a larger entity such as a vaccine sequence and/or a polypeptide comprising more than one T cell epitope. The presented peptide or T cell epitope is produced following suitable processing.

T cell epitopes may be modified at one or more residues that are not essential for TCR recognition or for binding to MHC. Such modified T cell epitopes may be considered immunologically equivalent.

Preferably a T cell epitope when presented by MHC and recognized by a T cell receptor is able to induce in the presence of appropriate co-stimulatory signals, clonal expansion of the T cell carrying the T cell receptor specifically recognizing the peptide/MHC-complex.

Preferably, a T cell epitope comprises an amino acid sequence substantially corresponding to the amino acid sequence of a fragment of an antigen. Preferably, said fragment of an antigen is an MHC class I and/or class II presented peptide.

A T cell epitope according to the invention preferably relates to a portion or fragment of an antigen which is capable of stimulating an immune response, preferably a cellular response against the antigen or cells characterized by expression of the antigen and preferably by presentation of the antigen such as diseased cells, in particular cancer cells. Preferably, a T cell epitope is capable of stimulating a cellular response against a cell characterized by presentation of an antigen with class I MHC and preferably is capable of stimulating an antigen-responsive cytotoxic T-lymphocyte (CTL).

"Antigen processing" or "processing" refers to the degradation of a peptide, polypeptide or protein into procession products, which are fragments of said peptide, polypeptide or protein (e.g., the degradation of a polypeptide into peptides) and the association of one or more of these fragments (e.g., via binding) with MHC molecules for presentation by cells, preferably antigen presenting cells, to specific T cells.

"Antigen presenting cells" (APC) are cells which present peptide fragments of protein antigens in association with MHC molecules on their cell surface. Some APCs may activate antigen specific T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells. Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity. Dendritic cells are conveniently categorized as "immature" and "mature" cells, which can be used as a simple way to discriminate between two well characterized phenotypes. However, this nomenclature should not be construed to exclude all possible intermediate stages of differentiation. Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB). Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Non-professional antigen-presenting cells do not constitutively express the MHC class II proteins required for interaction with naive T cells; these are expressed only upon stimulation of the non-professional antigen-presenting cells by certain cytokines such as IFNγ.

Antigen presenting cells can be loaded with MHC class I presented peptides by transducing the cells with nucleic acid, preferably RNA, encoding a peptide or polypeptide comprising the peptide to be presented, e.g. a nucleic acid encoding an antigen or polypeptide used for vaccination.

In some embodiments, a pharmaceutical composition or vaccine comprising a nucleic acid delivery vehicle that targets a dendritic or other antigen presenting cell may be administered to a patient, resulting in transfection that occurs in vivo. In vivo transfection of dendritic cells, for example, may generally be performed using any methods known in the art, such as those described in WO 97/24447, or the gene gun approach described by Mahvi et al., Immunology and cell Biology 75: 456-460, 1997.

According to the invention, the term "antigen presenting cell" also includes target cells.

"Target cell" shall mean a cell which is a target for an immune response such as a cellular immune response. Target cells include cells that present an antigen, i.e. a peptide fragment derived from an antigen, and include any undesirable cell such as a cancer cell. In preferred embodiments, the target cell is a cell expressing an antigen as described herein and preferably presenting said antigen with class I MHC.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence.

The term "immunoreactive cell" in the context of the present invention relates to a cell which exerts effector functions during an immune reaction. An "immunoreactive cell" preferably is capable of binding an antigen or a cell characterized by presentation of an antigen or a peptide fragment thereof (e.g. a T cell epitope) and mediating an immune response. For example, such cells secrete cytokines and/or chemokines, secrete antibodies, recognize cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably $CD4^+$ and/or $CD8^+$ T cells.

Preferably, an "immunoreactive cell" recognizes an antigen or a peptide fragment thereof with some degree of specificity, in particular if presented in the context of MHC molecules such as on the surface of antigen presenting cells or diseased cells such as cancer cells. Preferably, said recognition enables the cell that recognizes an antigen or a peptide fragment thereof to be responsive or reactive. If the cell is a helper T cell ($CD4^+$ T cell) bearing receptors that recognize an antigen or a peptide fragment thereof in the context of MHC class II molecules such responsiveness or reactivity may involve the release of cytokines and/or the activation of $CD8^+$ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-$\gamma$ and TNF-$\alpha$, up-regulation of activation markers such as CD44 and CD69, and specific cytolytic killing of antigen expressing target cells. CTL responsiveness may also be determined using an artificial reporter that accurately indicates CTL responsiveness. Such CTL that recognize an antigen or an antigen fragment and are responsive or reactive are also termed "antigen-responsive CTL" herein. If the cell is a B cell such responsiveness may involve the release of immunoglobulins.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCR$\alpha$ and TCR$\beta$) genes and are called $\alpha$- and $\beta$-TCR chains. $\gamma\delta$ T cells (gamma delta T cells) represent a small subset of T cells that possess a distinct T cell receptor (TCR) on their surface. However, in $\gamma\delta$ T cells, the TCR is made up of one γ-chain and one δ-chain. This group of T cells is much less common (2% of total T cells) than the αβ T cells.

The first signal in activation of T cells is provided by binding of the T cell receptor to a short peptide presented by the MHC on another cell. This ensures that only a T cell with a TCR specific to that peptide is activated. The partner cell is usually an antigen presenting cell such as a professional antigen presenting cell, usually a dendritic cell in the case of naïve responses, although B cells and macrophages can be important APCs.

T cells described herein may also comprise an artificial T cell receptor, e.g. instead of or in addition to the T cell's own T cell receptor. Such T cells do not necessarily require processing and presentation of an antigen for recognition of the target cell but rather may recognize preferably with specificity any antigen present on a target cell. Preferably, said artificial T cell receptor is expressed on the surface of the cells. For the purpose of the present invention T cells comprising an artificial T cell receptor are comprised by the term "T cell" as used herein.

According to the invention the term "artificial T cell receptor" is synonymous with the terms "chimeric T cell receptor" and "chimeric antigen receptor (CAR)". These terms relate to engineered receptors, which confer an arbitrary specificity such as the specificity of a monoclonal antibody onto an immune effector cell such as a T cell. In this way, a large number of cancer-specific T cells can be generated for adoptive cell transfer.

In one embodiment, a single-chain variable fragment (scFv) derived from a monoclonal antibody is fused to CD3-zeta transmembrane and endodomain. Such molecules result in the transmission of a zeta signal in response to recognition by the scFv of its antigen target on a target cell and killing of the target cell that expresses the target antigen. Antigen recognition domains which also may be used include among others T-cell receptor (TCR) alpha and beta single chains. In fact almost anything that binds a given target with high affinity can be used as an antigen recognition domain.

Following antigen recognition, receptors cluster and a signal is transmitted to the cell. The most commonly used endodomain component is CD3-zeta. This transmits an activation signal to the T cell after antigen is bound.

Adoptive cell transfer therapy with CAR-engineered T cells expressing chimeric antigen receptors is a promising anti-cancer therapeutic as CAR-modified T cells can be engineered to target virtually any tumor antigen. For example, patient's T cells may be genetically engineered to express CARs specifically directed towards antigens on the patient's tumor cells, then infused back into the patient.

According to the present invention, a molecule is capable of binding to a target if it has a significant affinity for said predetermined target and binds to said predetermined target in standard assays. "Affinity" or "binding affinity" is often measured by equilibrium dissociation constant ($K_D$). A molecule is not (substantially) capable of binding to a target if it has no significant affinity for said target and does not bind significantly to said target in standard assays.

Cytotoxic T lymphocytes may be generated in vivo by incorporation of an antigen, an immunogenic peptide fragment thereof or polypeptide comprising such immunogenic peptide fragment into antigen-presenting cells in vivo. The antigen, peptide fragment or polypeptide may be represented as protein, as DNA (e.g. within a vector) or as RNA. The antigen or polypeptide may be processed to produce a peptide partner for the MHC molecule, while a fragment thereof may be presented without the need for further processing. The latter is the case in particular, if these can bind to MHC molecules. In general, administration to a patient by intradermal injection is possible. However, injection may also be carried out intranodally into a lymph node (Maloy et al. (2001), Proc Natl Acad Sci USA 98:3299-303). The resulting cells present the complex of interest and are recognized by autologous cytotoxic T lymphocytes which then propagate.

Specific activation of CD4+ or CD8+ T cells may be detected in a variety of ways. Methods for detecting specific T cell activation include detecting the proliferation of T cells, the production of cytokines (e.g., lymphokines), or the generation of cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity.

By "cell characterized by presentation of an antigen" or "cell presenting an antigen" or similar expressions is meant a cell such as a diseased cell, e.g. a cancer cell, or an antigen presenting cell presenting the antigen it expresses or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

By "fragment of an antigen which is presented" or similar expressions is meant that the fragment can be presented by MHC class I or class II, preferably MHC class I, e.g. when added directly to antigen presenting cells. In one embodiment, the fragment is a fragment which is naturally presented by cells expressing an antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "immune effector functions" in the context of the present invention includes any functions mediated by components of the immune system that result, for example, in the killing of tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell ($CD4^+$ T cell) the recognition of an antigen or an antigen fragment in the context of MHC class II molecules by T cell receptors, the release of cytokines and/or the activation of $CD8^+$ lymphocytes (CTLs) and/or B-cells, and in the case of CTL the recognition of an antigen or an antigen fragment in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

According to the invention, epitopes may have amino acid modifications which may result from mutations in the nucleic acid of a cell. Such mutations may be identified by known sequencing techniques.

In one embodiment, the mutations are cancer specific somatic mutations in a tumor specimen of a cancer patient which may be determined by identifying sequence differences between the genome, exome and/or transcriptome of a tumor specimen and the genome, exome and/or transcriptome of a non-tumorigenous specimen.

According to the invention a tumor specimen relates to any sample such as a bodily sample derived from a patient containing or being expected of containing tumor or cancer cells. The bodily sample may be any tissue sample such as blood, a tissue sample obtained from the primary tumor or from tumor metastases or any other sample containing tumor or cancer cells. Preferably, a bodily sample is blood and cancer specific somatic mutations or sequence differences are determined in one or more circulating tumor cells (CTCs) contained in the blood. In another embodiment, a tumor specimen relates to one or more isolated tumor or cancer cells such as circulating tumor cells (CTCs) or a sample containing one or more isolated tumor or cancer cells such as circulating tumor cells (CTCs).

A non-tumorigenous specimen relates to any sample such as a bodily sample derived from a patient or another individual which preferably is of the same species as the patient, preferably a healthy individual not containing or not being expected of containing tumor or cancer cells. The bodily sample may be any tissue sample such as blood or a sample from a non-tumorigenous tissue.

The invention may involve the determination of the cancer mutation signature of a patient. The term "cancer mutation signature" may refer to all cancer mutations present in one or more cancer cells of a patient or it may refer to only a portion of the cancer mutations present in one or more cancer cells of a patient. Accordingly, the present invention may involve the identification of all cancer specific mutations present in one or more cancer cells of a patient or it may involve the identification of only a portion of the cancer specific mutations present in one or more cancer cells of a patient.

Preferably, the mutations identified according to the present invention are non-synonymous mutations, preferably non-synonymous mutations of proteins expressed in a tumor or cancer cell.

In one embodiment, cancer specific somatic mutations or sequence differences are determined in the genome, preferably the entire genome, of a tumor specimen. Thus, the invention may comprise identifying the cancer mutation signature of the genome, preferably the entire genome of one or more cancer cells. In one embodiment, the step of identifying cancer specific somatic mutations in a tumor specimen of a cancer patient comprises identifying the genome-wide cancer mutation profile.

In one embodiment, cancer specific somatic mutations or sequence differences are determined in the exome, preferably the entire exome, of a tumor specimen. Thus, the invention may comprise identifying the cancer mutation signature of the exome, preferably the entire exome of one or more cancer cells. In one embodiment, the step of identifying cancer specific somatic mutations in a tumor specimen of a cancer patient comprises identifying the exome-wide cancer mutation profile.

In one embodiment, cancer specific somatic mutations or sequence differences are determined in the transcriptome, preferably the entire transcriptome, of a tumor specimen. Thus, the invention may comprise identifying the cancer mutation signature of the transcriptome, preferably the entire transcriptome of one or more cancer cells. In one embodiment, the step of identifying cancer specific somatic mutations in a tumor specimen of a cancer patient comprises identifying the transcriptome-wide cancer mutation profile.

In one embodiment, the step of identifying cancer specific somatic mutations or identifying sequence differences comprises single cell sequencing of one or more, preferably 2, 3, 4, 5, 6, 7, 8, 9, 10, 11, 12, 13, 14, 15, 16, 17, 18, 19, 20 or even more cancer cells. Thus, the invention may comprise identifying a cancer mutation signature of said one or more cancer cells. In one embodiment, the cancer cells are circulating tumor cells. The cancer cells such as the circulating tumor cells may be isolated prior to single cell sequencing.

In one embodiment, the step of identifying cancer specific somatic mutations or identifying sequence differences involves using next generation sequencing (NGS).

In one embodiment, the step of identifying cancer specific somatic mutations or identifying sequence differences comprises sequencing genomic DNA and/or RNA of the tumor specimen.

To reveal cancer specific somatic mutations or sequence differences the sequence information obtained from the tumor specimen is preferably compared with a reference such as sequence information obtained from sequencing nucleic acid such as DNA or RNA of normal non-cancerous cells such as germline cells which may either be obtained from the patient or a different individual. In one embodiment, normal genomic germline DNA is obtained from peripheral blood mononuclear cells (PBMCs)

The term "genome" relates to the total amount of genetic information in the chromosomes of an organism or a cell.

The term "exome" refers to part of the genome of an organism formed by exons, which are coding portions of expressed genes. The exome provides the genetic blueprint used in the synthesis of proteins and other functional gene products. It is the most functionally relevant part of the genome and, therefore, it is most likely to contribute to the phenotype of an organism. The exome of the human genome is estimated to comprise 1.5% of the total genome (Ng, P C et al., *PLoS Gen.*, 4(8): 1-15, 2008).

The term "transcriptome" relates to the set of all RNA molecules, including mRNA, r RNA, tRNA, and other non-coding RNA produced in one cell or a population of cells. In context of the present invention the transcriptome means the set of all RNA molecules produced in one cell, a population of cells, preferably a population of cancer cells, or all cells of a given individual at a certain time point.

A "nucleic acid" is according to the invention preferably deoxyribonucleic acid (DNA) or ribonucleic acid (RNA), more preferably RNA, most preferably in vitro transcribed RNA (IVT RNA) or synthetic RNA. Nucleic acids include according to the invention genomic DNA, cDNA, mRNA, recombinantly produced and chemically synthesized molecules. According to the invention, a nucleic acid may be present as a single-stranded or double-stranded and linear or covalently circularly closed molecule. A nucleic acid can, according to the invention, be isolated. The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, in particular, in the form of RNA which can be prepared by in vitro transcription from a DNA template. The RNA can moreover be modified before application by stabilizing sequences, capping, and polyadenylation.

The term "genetic material" includes isolated nucleic acid, either DNA or RNA, a section of a double helix, a section of a chromosome, or an organism's or cell's entire genome, in particular its exome or transcriptome.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. Preferably a mutation is a non-synonymous mutation. The term "non-synonymous mutation" refers to a mutation, preferably a nucleotide substitution, which does result in an amino acid change such as an amino acid substitution in the translation product.

According to the invention, the term "mutation" includes point mutations, Indels, fusions, chromothripsis and RNA edits.

According to the invention, the term "Indel" describes a special mutation class, defined as a mutation resulting in a colocalized insertion and deletion and a net gain or loss in nucleotides. In coding regions of the genome, unless the length of an indel is a multiple of 3, they produce a frameshift mutation. Indels can be contrasted with a point mutation; where an Indel inserts and deletes nucleotides from a sequence, a point mutation is a form of substitution that replaces one of the nucleotides.

Fusions can generate hybrid genes formed from two previously separate genes. It can occur as the result of a translocation, interstitial deletion, or chromosomal inversion. Often, fusion genes are oncogenes. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. Oncogenic fusion transcripts may also be caused by trans-splicing or read-through events.

According to the invention, the term "chromothripsis" refers to a genetic phenomenon by which specific regions of the genome are shattered and then stitched together via a single devastating event.

According to the invention, the term "RNA edit" or "RNA editing" refers to molecular processes in which the information content in an RNA molecule is altered through a chemical change in the base makeup. RNA editing includes nucleoside modifications such as cytidine (C) to uridine (U) and adenosine (A) to inosine (I) deaminations, as well as non-templated nucleotide additions and insertions. RNA editing in mRNAs effectively alters the amino acid sequence of the encoded protein so that it differs from that predicted by the genomic DNA sequence.

The term "cancer mutation signature" refers to a set of mutations which are present in cancer cells when compared to non-cancerous reference cells.

According to the invention, a "reference" may be used to correlate and compare the results obtained from a tumor specimen. Typically the "reference" may be obtained on the basis of one or more normal specimens, in particular specimens which are not affected by a cancer disease, either obtained from a patient or one or more different individuals, preferably healthy individuals, in particular individuals of the same species. A "reference" can be determined empirically by testing a sufficiently large number of normal specimens.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA". The term "mRNA" means "messenger-RNA" and relates to a "transcript" which is generated by using a DNA template and encodes a peptide or polypeptide. Typically, an mRNA comprises a 5'-UTR, a protein coding region, and a 3'-UTR. mRNA only possesses limited half-life in cells and in vitro. In the context of the present invention, mRNA may be generated by in vitro transcription from a DNA template. The in vitro transcription methodology is known to the skilled person. For example, there is a variety of in vitro transcription kits commercially available.

According to the invention, the stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

Providing an RNA with a 5'-cap or 5'-cap analog may be achieved by in vitro transcription of a DNA template in presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

In addition, incorporation of a 3'-non translated region (UTR) into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced. In one particular embodiment the 3'-non translated region is derived from the human β-globin gene.

A combination of the above described modifications, i.e. incorporation of a poly-A sequence, unmasking of a poly-A sequence and incorporation of one or more 3'-non translated regions, has a synergistic influence on the stability of RNA and increase in translation efficiency.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The term "expression" is used according to the invention in its most general meaning and comprises the production of RNA and/or peptides, polypeptides or proteins, e.g. by transcription and/or translation. With respect to RNA, the term "expression" or "translation" relates in particular to the production of peptides, polypeptides or proteins. It also comprises partial expression of nucleic acids. Moreover, expression can be transient or stable. According to the invention, a tumor antigen is expressed in a cell if the tumor antigen can be detected in the cell or a lysate thereof by conventional techniques for protein detection such as techniques using antibodies specifically binding to the tumor antigen. Preferably, a tumor antigen is expressed in a cell if T cells are able to bind to a peptide fragment derived from the tumor antigen presented on the cell in the context of MHC molecules and preferably are able to exert immune effector functions on the cell.

According to the invention, the term expression also includes an "aberrant expression" or "abnormal expression". "Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide, polypeptide or protein.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5' untranscribed regulatory sequences comprise a promoter region that includes a promoter sequence for transcriptional control of the functionally bound gene. Regulatory sequences can also comprise enhancer sequences or upstream activator sequences.

Preferably, according to the invention, RNA to be expressed in a cell is introduced into said cell. In one embodiment of the methods according to the invention, the RNA that is to be introduced into a cell is obtained by in vitro transcription of an appropriate DNA template.

According to the invention, terms such as "RNA capable of expressing" and "RNA encoding" are used interchangeably herein and with respect to a particular peptide or polypeptide mean that the RNA, if present in the appropriate environment, preferably within a cell, can be expressed to produce said peptide or polypeptide. Preferably, RNA according to the invention is able to interact with the cellular translation machinery to provide the peptide or polypeptide it is capable of expressing.

Terms such as "transferring", "introducing" or "transfecting" are used interchangeably herein and relate to the introduction of nucleic acids, in particular exogenous or heterologous nucleic acids, in particular RNA into a cell. According to the present invention, the cell can form part of an organ, a tissue and/or an organism. According to the present invention, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. The present invention also envisions the repeated introduction of nucleic acids into cells to allow sustained expression for extended time periods.

Cells can be transfected with any carriers with which RNA can be associated, e.g. by forming complexes with the RNA or forming vesicles in which the RNA is enclosed or encapsulated, resulting in increased stability of the RNA compared to naked RNA. Carriers useful according to the invention include, for example, lipid-containing carriers such as cationic lipids, liposomes, in particular cationic liposomes, and micelles, and nanoparticles. Cationic lipids may form complexes with negatively charged nucleic acids. Any cationic lipid may be used according to the invention.

Preferably, the introduction of RNA which encodes a peptide or polypeptide into a cell, in particular into a cell present in vivo, results in expression of said peptide or polypeptide in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., *E. coli*) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii)

incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage.

A cell which comprises a nucleic acid molecule preferably expresses the peptide or polypeptide encoded by the nucleic acid.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

Terms such as "reducing" or "inhibiting" relate to the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increasing", "enhancing", "promoting" or "prolonging" preferably relate to an increase, enhancement, promotion or prolongation by about at least 10%, preferably at least 20%, preferably at least 30%, preferably at least 40%, preferably at least 50%, preferably at least 80%, preferably at least 100%, preferably at least 200% and in particular at least 300%. These terms may also relate to an increase, enhancement, promotion or prolongation from zero or a non-measurable or non-detectable level to a level of more than zero or a level which is measurable or detectable.

According to the invention, the term "vaccine" relates to a pharmaceutical preparation (pharmaceutical composition) or product that upon administration induces an immune response, in particular a cellular immune response, which recognizes and attacks a pathogen or a diseased cell such as a cancer cell. A vaccine may be used for the prevention or treatment of a disease. The term "personalized cancer vaccine" or "individualized cancer vaccine" concerns a particular cancer patient and means that a cancer vaccine is adapted to the needs or special circumstances of an individual cancer patient.

In one embodiment, a vaccine provided according to the invention may comprise one or more peptides or polypeptides comprising immunogenic epitopes such as T cell epitopes or a nucleic acid, preferably RNA, encoding said peptides or polypeptides.

The cancer vaccines provided according to the invention when administered to a patent preferably provide one or more T cell epitopes suitable for stimulating, priming and/or expanding T cells specific for the patients tumor. The T cells are preferably directed against cells expressing antigens from which the T cell epitopes are derived. Thus, the vaccines described herein are preferably capable of inducing or promoting a cellular response, preferably cytotoxic T cell activity, against a cancer disease characterized by presentation of one or more tumor antigens with class I MHC.

In one embodiment, a vaccine provided according to the invention relates to a vaccine which when administered to a patent preferably provides one or more T cell epitopes, such as 2 or more, 5 or more, 10 or more, 15 or more, 20 or more, 25 or more, 30 or more and preferably up to 60, up to 55, up to 50, up to 45, up to 40, up to 35 or up to 30 T cell epitopes. Presentation of these epitopes by cells of a patient, in particular antigen presenting cells, preferably results in T cells targeting the epitopes when bound to MHC and thus, the patient's tumor, preferably the primary tumor as well as tumor metastases, expressing antigens from which the T cell epitopes are derived and presenting the same epitopes on the surface of the tumor cells.

Epitopes provided by a vaccine of the invention are preferably present in the form of a polypeptide comprising said epitopes such as a polyepitopic polypeptide or a nucleic acid, in particular RNA, encoding said polypeptide. Furthermore, the epitopes may be present in the polypeptide in the form of a vaccine sequence, i.e. present in their natural sequence context, e.g. flanked by amino acid sequences also flanking said epitopes in the naturally occurring protein. Such flanking sequences each may comprise 5 or more, 10 or more, 15 or more, 20 or more and preferably up to 50, up to 45, up to 40, up to 35 or up to 30 amino acids and may flank the epitope sequence N-terminally and/or C-terminally. Thus, a vaccine sequence may comprise 20 or more, 25 or more, 30 or more, 35 or more, 40 or more and preferably up to 50, up to 45, up to 40, up to 35 or up to 30 amino acids. In one embodiment, the epitopes and/or vaccine sequences are lined up in the polypeptide head-to-tail.

In one embodiment, the epitopes and/or vaccine sequences are spaced by linkers, in particular neutral linkers. The term "linker" according to the invention relates to a peptide added between two peptide domains such as epitopes or vaccine sequences to connect said peptide domains. There is no particular limitation regarding the linker sequence. However, it is preferred that the linker sequence reduces steric hindrance between the two peptide domains, is well translated, and supports or allows processing of the epitopes. Furthermore, the linker should have no or only little immunogenic sequence elements. Linkers preferably should not create non-endogenous epitopes like those generated from the junction suture between adjacent epitopes, which might generate unwanted immune reactions. Therefore, the polyepitopic vaccine should preferably contain linker sequences which are able to reduce the number of unwanted MHC binding junction epitopes. Hoyt et al. (*EMBO J.* 25(8), 1720-9, 2006) and Zhang et al. (*J. Biol. Chem.*, 279(10), 8635-41, 2004) have shown that glycine-rich sequences impair proteasomal processing and thus the use of glycine rich linker sequences act to minimize the number of linker-contained peptides that can be processed by the proteasome. Furthermore, glycine was observed to inhibit a strong binding in MHC binding groove positions (Abastado et al., *J. Immunol.* 151(7), 3569-75, 1993). Schlessinger et al. (*Proteins*, 61(1), 115-26, 2005) had found that amino acids glycine and serine included in an amino acid sequence result in a more flexible protein that is more efficiently translated and processed by the proteasome, enabling better access to the encoded epitopes. The linker each may comprise 3 or more, 6 or more, 9 or more, 10 or more, 15 or more, 20 or more and preferably up to 50, up to 45, up to 40, up to 35 or up to 30 amino acids. Preferably the linker is enriched in glycine and/or serine amino acids. Preferably, at least 50%, at least 60%, at least 70%, at least 80%, at least 90%, or at least 95% of the amino acids of the linker are glycine and/or serine. In one preferred embodiment, a linker is substantially composed of the amino acids glycine and serine. In one embodiment, the linker comprises the amino acid sequence $(GGS)_a(GSS)_b(GGG)_c(SSG)_d$ (GSG)$_e$ wherein a, b, c, d and e is independently a number selected from 0, 1, 2, 3, 4, 5, 6, 7, 8, 9, 10, 11, 12, 13, 14, 15, 16, 17, 18, 19, or 20 and wherein a+b+c+d+e are different from 0 and preferably are 2 or more, 3 or more, 4 or more or 5 or more. In one embodiment, the linker comprises the sequence GGSGGGGSG.

In one particularly preferred embodiment, a polypeptide incorporating one or more epitopes such as a polyepitopic polypeptide according to the present invention is administered to a patient in the form of a nucleic acid, preferably RNA such as in vitro transcribed or synthetic RNA, which may be expressed in cells of a patient such as antigen presenting cells to produce the polypeptide. The present invention also envisions the administration of one or more multiepitopic polypeptides which for the purpose of the present invention are comprised by the term "polyepitopic polypeptide", preferably in the form of a nucleic acid, preferably RNA such as in vitro transcribed or synthetic RNA, which may be expressed in cells of a patient such as antigen presenting cells to produce the one or more polypeptides. In the case of an administration of more than one multiepitopic polypeptide the epitopes provided by the different multiepitopic polypeptides may be different or partially overlapping. Once present in cells of a patient such as antigen presenting cells the polypeptide according to the invention is processed to produce the epitopes. Administration of a vaccine provided according to the invention may provide MHC class II-presented epitopes that are capable of eliciting a CD4+ helper T cell response against cells expressing antigens from which the MHC presented epitopes are derived. Alternatively or additionally, administration of a vaccine provided according to the invention may provide MHC class I-presented epitopes that are capable of eliciting a CD8+ T cell response against cells expressing antigens from which the MHC presented epitopes are derived. Furthermore, administration of a vaccine provided according to the invention may provide one or more neo-epitopes (including known neo-epitopes and neo-epitopes identified according to the invention) as well as one or more epitopes not containing cancer specific somatic mutations. In one embodiment, administration of a vaccine provided according to the invention provides neo-epitopes that are MHC class II-presented epitopes and/or are capable of eliciting a CD4+ helper T cell response against cells expressing antigens from which the MHC presented epitopes are derived as well as epitopes not containing cancer-specific somatic mutations that are MHC class I-presented epitopes and/or are capable of eliciting a CD8+ T cell response against cells expressing antigens from which the MHC presented epitopes are derived. In one embodiment, the neo-epitopes and epitopes not containing cancer-specific somatic mutations have a synergistic effect in the treatment of cancer. Preferably, a vaccine provided according to the invention is useful for polyepitopic stimulation of cytotoxic and/or helper T cell responses.

The vaccine provided according to the invention may be a recombinant vaccine.

The term "recombinant" in the context of the present invention means "made through genetic engineering". Preferably, a "recombinant entity" such as a recombinant polypeptide in the context of the present invention is not occurring naturally, and preferably is a result of a combination of entities such as amino acid or nucleic acid sequences which are not combined in nature. For example, a recombinant polypeptide in the context of the present invention may contain several amino acid sequences such as epitopes or vaccine sequences derived from different proteins such as CXorf61, CAGE1 and/or PRAME or different portions of the same protein fused together, e.g., by peptide bonds or appropriate linkers.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

Agents, compositions and methods described herein can be used to treat a subject with a disease, e.g., a disease characterized by the presence of diseased cells expressing one or more antigens and presenting a fragment thereof. Particularly preferred diseases are cancer diseases. Agents, compositions and methods described herein may also be used for immunization or vaccination to prevent a disease described herein.

According to the invention, the term "disease" refers to any pathological state, including cancer diseases, in particular those forms of cancer diseases described herein.

The term "normal" refers to the healthy state or the conditions in a healthy subject or tissue, i.e., non-pathological conditions, wherein "healthy" preferably means non-cancerous.

"Disease involving cells expressing an antigen" means according to the invention that expression of the antigen in cells of a diseased tissue or organ is detected. Expression in cells of a diseased tissue or organ may be increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing an antigen include cancer diseases.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not. Malignancy, malignant neoplasm, and malignant tumor are essentially synonymous with cancer.

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli, it usually causes a lump or tumor. Neoplasms may be benign, pre-malignant or malignant.

"Growth of a tumor" or "tumor growth" according to the invention relates to the tendency of a tumor to increase its size and/or to the tendency of tumor cells to proliferate.

For purposes of the present invention, the terms "cancer" and "cancer disease" are used interchangeably with the terms "tumor" and "tumor disease".

Cancers are classified by the type of cell that resembles the tumor and, therefore, the tissue presumed to be the origin of the tumor. These are the histology and the location, respectively.

The term "cancer" according to the invention comprises carcinomas, adenocarcinomas, blastomas, leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases and relapse of cancer.

In one particularly preferred embodiment, the term "cancer" according to the invention relates to "breast cancer"

The term "breast cancer" relates to a type of cancer originating from breast tissue, most commonly from the inner lining of milk ducts or the lobules that supply the ducts with milk. Cancers originating from ducts are known as ductal carcinomas, while those originating from lobules are known as lobular carcinomas. Occasionally, breast cancer presents as metastatic disease. Common sites of metastasis include bone, liver, lung and brain. Breast cancer occurs in humans and other mammals. While the overwhelming majority of human cases occur in women, male breast cancer can also occur.

Treatment of breast cancer may include surgery, medications (hormonal therapy and chemotherapy), radiation and/or immunotherapy.

Breast cancer cells may or may not have three important receptors: estrogen receptor (ER), progesterone receptor (PR), and Her2/neu (HER2). A particularly preferred form of breast cancer according to the invention is triple-negative breast cancer. The term "triple-negative breast cancer" refers to any breast cancer that does not express or does not overexpress the genes for estrogen receptor (ER), progesterone receptor (PR) and HER2.

The three main groups of medications used for adjuvant breast cancer treatment are hormone blocking therapy, chemotherapy, and monoclonal antibodies.

Hormone Blocking Therapy

ER positive/PR positive breast cancers can be treated with drugs that either block the receptors, e.g. tamoxifen (Nolvadex), or alternatively block the production of estrogen with an aromatase inhibitor, e.g. anastrozole (Arimidex) or letrozole (Femara). Aromatase inhibitors, however, are only suitable for post-menopausal patients. This is because the active aromatase in postmenopausal women is different from the prevalent form in premenopausal women, and therefore these agents are ineffective in inhibiting the predominant aromatase of premenopausal women.

Chemotherapy

Chemotherapy is predominately used for stage 2-4 disease and is particularly beneficial in ER negative breast cancer. They are given in combinations, usually for 3-6 months. One of the most common treatments is cyclophosphamide plus doxorubicin (adriamycin), known as AC. Most chemotherapy medications work by destroying fast-growing and/or fast-replicating cancer cells either by causing DNA damage upon replication or other mechanisms; these drugs also damage fast-growing normal cells where they cause serious side effects. Damage to the heart muscle is the most dangerous complication of doxorubicin. Sometimes a taxane drug, such as docetaxel, is added, and the regime is then known as CAT; taxane attacks the microtubules in cancer cells. Another common treatment, which produces equivalent results, is cyclophosphamide, methotrexate, and fluorouracil (CMF).

Monoclonal Antibodies

Trastuzumab (Herceptin), a monoclonal antibody to HER2, is only effective in patients with HER2 amplification/overexpression. Trastuzumab, however, is expensive, and approximately 2% of patients suffer significant heart damage. Other monoclonal antibodies are also undergoing clinical trials. Between 25 and thirty percent of breast cancers have an amplification of the HER2 gene or overexpression of its protein product. Overexpression of this receptor in breast cancer is associated with increased disease recurrence and worse prognosis.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if breast cancer metastasizes to the liver, the secondary tumor is made up of abnormal breast cells, not of abnormal liver cells. The tumor in the liver is then called metastatic breast cancer, not liver cancer.

The term "circulating tumor cells" or "CTCs" relates to cells that have detached from a primary tumor or tumor metastases and circulate in the bloodstream. CTCs may constitute seeds for subsequent growth of additional tumors (metastasis) in different tissues. Circulating tumor cells are found in frequencies in the order of 1-10 CTC per mL of whole blood in patients with metastatic disease. Research methods have been developed to isolate CTC. Several research methods have been described in the art to isolate CTCs, e.g. techniques which use of the fact that epithelial cells commonly express the cell adhesion protein EpCAM, which is absent in normal blood cells. Immunomagnetic bead-based capture involves treating blood specimens with antibody to EpCAM that has been conjugated with magnetic particles, followed by separation of tagged cells in a magnetic field. Isolated cells are then stained with antibody to another epithelial marker, cytokeratin, as well as a common leukocyte marker CD45, so as to distinguish rare CTCs from contaminating white blood cells. This robust and semi-automated approach identifies CTCs with an average yield of approximately 1 CTC/mL and a purity of 0.1% (Allard et al., 2004: *Clin Cancer Res* 10, 6897-6904). A second method for isolating CTCs uses a microfluidic-based CTC capture device which involves flowing whole blood through a chamber embedded with 80,000 microposts that have been rendered functional by coating with antibody to EpCAM. CTCs are then stained with secondary antibodies against either cytokeratin or tissue specific markers, such as PSA in prostate cancer or HER2 in breast cancer and are visualized by automated scanning of microposts in multiple planes along three dimensional coordinates. CTC-chips are able to identifying cytokerating-positive circulating tumor cells in patients with a median yield of 50 cells/ml and purity ranging from 1-80% (Nagrath et al., 2007: *Nature* 450, 1235-1239). Another possibility for isolating CTCs is using the CellSearch™ Circulating Tumor Cell (CTC) Test from Veridex, LLC (Raritan, N.J.) which captures, identifies, and counts CTCs in a tube of blood. The CellSearch™ system is a U.S. Food and Drug Administration (FDA) approved methodology for enumeration of CTC in whole blood which is based on a combination of immunomagnetic labeling and automated digital microscopy. There are other methods for isolating CTCs described in the literature all of which can be used in conjunction with the present invention.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from breast tumor and has received a successful treatment a relapse or recurrence may be the occurrence of a breast tumor or the occurrence of a tumor at a site different to breast. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject. In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The term "immunotherapy" relates to a treatment involving a specific immune reaction.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

A prophylactic administration of an immunotherapy, for example, a prophylactic administration of a vaccine of the invention, preferably protects the recipient from the development of a disease. A therapeutic administration of an immunotherapy, for example, a therapeutic administration of a vaccine of the invention, may lead to the inhibition of the progress/growth of the disease. This comprises the deceleration of the progress/growth of the disease, in particular a disruption of the progression of the disease, which preferably leads to elimination of the disease.

Immunotherapy may be performed using any of a variety of techniques, in which agents provided herein function to remove diseased cells from a patient. Such removal may take place as a result of enhancing or inducing an immune response in a patient specific for an antigen or a cell expressing an antigen.

Within certain embodiments, immunotherapy may be active immunotherapy, in which treatment relies on the in vivo stimulation of the endogenous host immune system to react against diseased cells with the administration of immune response-modifying agents (such as polypeptides and nucleic acids as provided herein).

The agents and compositions provided herein may be used alone or in combination with conventional therapeutic regimens such as surgery, irradiation, chemotherapy and/or bone marrow transplantation (autologous, syngeneic, allogeneic or unrelated).

The term "immunization" or "vaccination" describes the process of treating a subject with the purpose of inducing an immune response for therapeutic or prophylactic reasons.

The term "in vivo" relates to the situation in a subject.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease, preferably a disease as described herein.

In one embodiment, a method of the invention is performed on a patient which is already diagnosed as having cancer.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "heterologous" is used to describe something consisting of multiple different elements. As an example, the transfer of one individual's bone marrow into a different individual constitutes a heterologous transplant. A heterologous gene is a gene derived from a source other than the subject.

As part of the composition for an immunization or a vaccination, preferably one or more agents as described herein are administered together with one or more adjuvants for inducing an immune response or for increasing an immune response. The term "adjuvant" relates to compounds which prolongs or enhances or accelerates an immune response. The composition of the present invention preferably exerts its effect without addition of adjuvants. Still, the composition of the present application may contain any known adjuvant. Adjuvants comprise a heterogeneous group of compounds such as oil emulsions (e.g., Freund's adjuvants), mineral compounds (such as alum), bacterial products (such as *Bordetella pertussis* toxin), liposomes, and immune-stimulating complexes. Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al, 1997, Mol. Cells 7: 178-186), incomplete Freund's adjuvants, complete Freund's adjuvants, vitamin E, montanid, alum, CpG oligonucleotides (Krieg et al., 1995, Nature 374: 546-549), and various water-in-oil emulsions which are prepared from biologically degradable oils such as squalene and/or tocopherol.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise co-stimulating molecules provided in the form of proteins or nucleic acids such as B7-1 and B7-2 (CD80 and CD86, respectively).

According to the invention, a sample is preferably a bodily sample. A bodily sample may be a tissue sample, including body fluids, and/or a cellular sample. Such bodily samples may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid or cell isolates.

The agents such as vaccines and compositions described herein may be administered via any conventional route, including by injection or infusion. The administration may be carried out, for example, orally, intravenously, intraperitoneally, intramuscularly, subcutaneously or transdermally. In one embodiment, administration is carried out intranodally such as by injection into a lymph node. Other forms of administration envision the in vitro transfection of antigen presenting cells such as dendritic cells with nucleic acids described herein followed by administration of the antigen presenting cells.

The agents described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The pharmaceutical compositions described herein are preferably sterile and contain an effective amount of the therapeutically active substance to generate the desired reaction or the desired effect.

The pharmaceutical compositions described herein are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition described herein may comprise a pharmaceutically compatible carrier. The term "carrier" refers to an organic or inorganic component, of a natural or synthetic nature, in which the active component is combined in order to facilitate application. According to the invention, the term "pharmaceutically compatible carrier" includes one or more compatible solid or liquid fillers, diluents or encapsulating substances, which are suitable for administration to a patient. The components of the pharmaceutical composition of the invention are usually such that no interaction occurs which substantially impairs the desired pharmaceutical efficacy.

The pharmaceutical compositions described herein may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

According to the invention, expression, such as expression of a tumor antigen or a set of tumor antigens, may be determined on the mRNA level (transcriptional level) or protein level (translational level), for example, by measuring the transcribed mRNA (e.g. via northern blot), by measuring the produced protein (e.g. via Western Blot), by directly or indirectly staining the protein (e.g. via immunohistochemistry) or by directly staining the mRNA (e.g. via in situ hybridization).

For example, according to the invention, determining the expression of a tumor antigen on the mRNA level (transcriptional level) may be carried out by detecting and/or determining the quantity of any of the nucleic acid sequences described herein for the respective tumor antigen. For example, determining the expression of CAGE1 may be carried out by detecting and/or determining the quantity of the nucleic acid sequence of SEQ ID NO: 41 or 42 or a variant thereof.

For example, according to the invention, determining the expression of a tumor antigen on the protein level (translational level) may be carried out by detecting and/or determining the quantity of any of the amino acid sequences described herein for the respective tumor antigen. For example, determining the expression of CAGE1 may be carried out by detecting and/or determining the quantity of the amino acid sequence of SEQ ID NO: 43 or 44 or a variant thereof.

In one preferred embodiment, the expression level is determined using an immunoassay, gel electrophoresis, spectrometry, chromatography, in situ hybridization, or a combination thereof.

According to the invention, an immunoassay may be selected from the group consisting of western blots, immunohistochemistry, radioimmunoassays, ELISA (enzyme linked immunosorbent assay), "sandwich" immunoassays, immunoprecipitation assays, precipitation reactions, gel diffusion precipitation reactions, immunodiffusion assays, agglutination assays, complement-fixation assays, immunoradiometric assays, fluorescent immunoassays, immunofluorescence, protein A immunoassays, flow cytometry and FACS analysis.

The present invention further relates to a kit comprising means such as reagents for determining the expression pattern of a set of tumor antigens, preferably in a sample isolated from a cancer patient. Said kit is useful for conducting the methods of the present invention.

In the context of the present invention, the term "kit of parts (in short: kit)" is understood to be any combination of at least some of the components identified herein, which are combined, coexisting spatially, to a functional unit, and which can contain further components.

In one embodiment, the kit comprises one or more means that specifically bind to tumor antigens of a set of tumor antigens.

Said means that specifically bind to tumor antigens may be antibodies or fragments thereof, which are capable of specially binding to an epitope or a suitable structural element of an antigen to be detected.

In other embodiments, said means may be nucleic acid. For nucleic acid detection, the kits generally comprise (but are not limited to) probes specific for mRNA encoding tumor antigens. For Quantitative PCR, the kits generally comprise pre-selected primers specific for nucleic acid sequences encoding tumor antigens. The Quantitative PCR kits may also comprise enzymes suitable for amplifying nucleic acids (e.g., polymerases such as Taq), and deoxynucleotides and buffers needed for the reaction mixture for amplification. The Quantitative PCR kits may also comprise probes specific for nucleic acid sequences encoding tumor antigens. In some embodiments, the Quantitative PCR kits also comprise components suitable for reverse-transcribing RNA including enzymes (e.g. reverse transcriptases) and primers for reverse transcription along with deoxynucleotides and buffers needed for the reverse transcription reaction.

In certain embodiments, said means are detectably labeled.

The antibody or antibody fragment may be bound to a solid support, e.g. a plastic surface, to allow binding and detection of a protein. For example, a microtiter plate can be used as a plastic surface. The detection of the binding can be effected by using a secondary antibody labeled with a detectable group. The detectable group can be an enzyme like horseradish peroxidase (HRP) or alkaline phosphatase detectable by adding a suitable substrate to produce a colour or a fluorescence signal.

Said kit may further comprise (i) a container, and/or (ii) a data carrier. Said container may be filled with one or more of the above mentioned means or reagents. Said data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronic data carrier. The access code may allow the access to a database, e.g. an internet database, a centralized, or a decentralized database. Said data carrier may comprise instructions for the use of the kit in the methods of the invention.

Additionally or alternatively, said kit may comprise materials desirable from a commercial and user standpoint including buffer(s), reagent(s) and/or diluent(s) for determining expression of protein or mRNA.

The above mentioned data carrier may comprise a threshold value or reference level of a protein or mRNA. In case that the data carrier comprises an access code which allows the access to a database, said threshold value or reference level is deposited in this database.

In addition, the data carrier may comprise information or instructions on how to carry out the methods of the present invention.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

For the purposes of the present invention, "variants" of an amino acid sequence comprise amino acid insertion variants, amino acid addition variants, amino acid deletion variants and/or amino acid substitution variants.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code.

Furthermore, a "variant" of a given nucleic acid sequence according to the invention includes nucleic acid sequences comprising single or multiple such as at least 2, at least 4, or at least 6 and preferably up to 3, up to 4, up to 5, up to 6, up to 10, up to 15, or up to 20 nucleotide substitutions, deletions and/or additions.

Preferably the degree of identity between a given nucleic acid sequence and a nucleic acid sequence which is a variant of said given nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence.

"Sequence identity" between two nucleic acid sequences indicates the percentage of nucleotides that are identical between the sequences.

The term "percentage identity" is intended to denote a percentage of nucleotides which are identical between the two sequences to be compared, obtained after the best alignment, this percentage being purely statistical and the differences between the two sequences being distributed randomly and over their entire length. Sequence comparisons between two nucleotide sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: Analysis of tumor antigen expression in breast cancer

Figure 2:
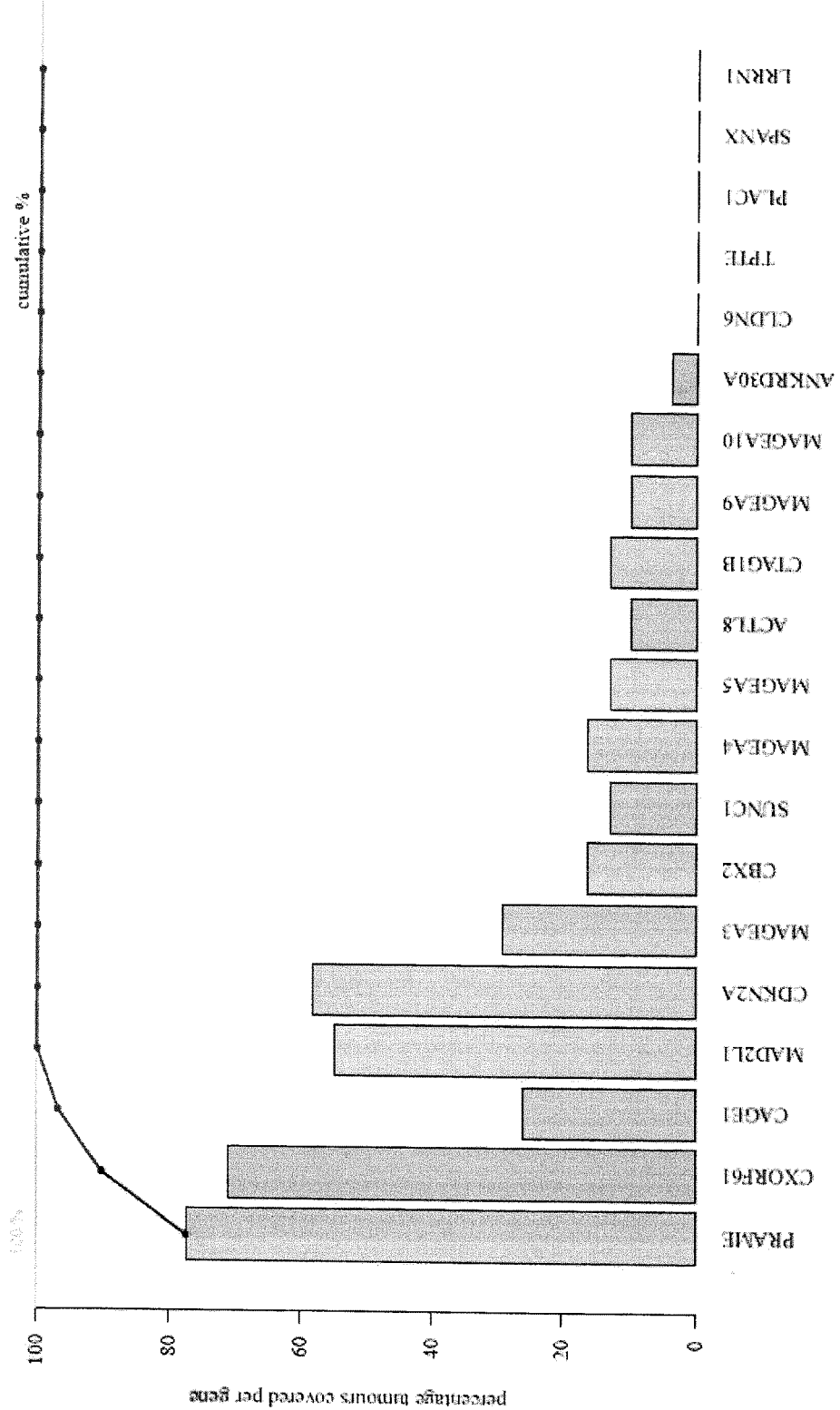

FIG. 2: Analysis of tumor antigen expression in triple-negative breast cancer (TNBC)

A combination of only three tumor antigens, CXorf61, CAGE1 and PRAME, is sufficient to represent 95% of the analysed samples.

Figure 3A:
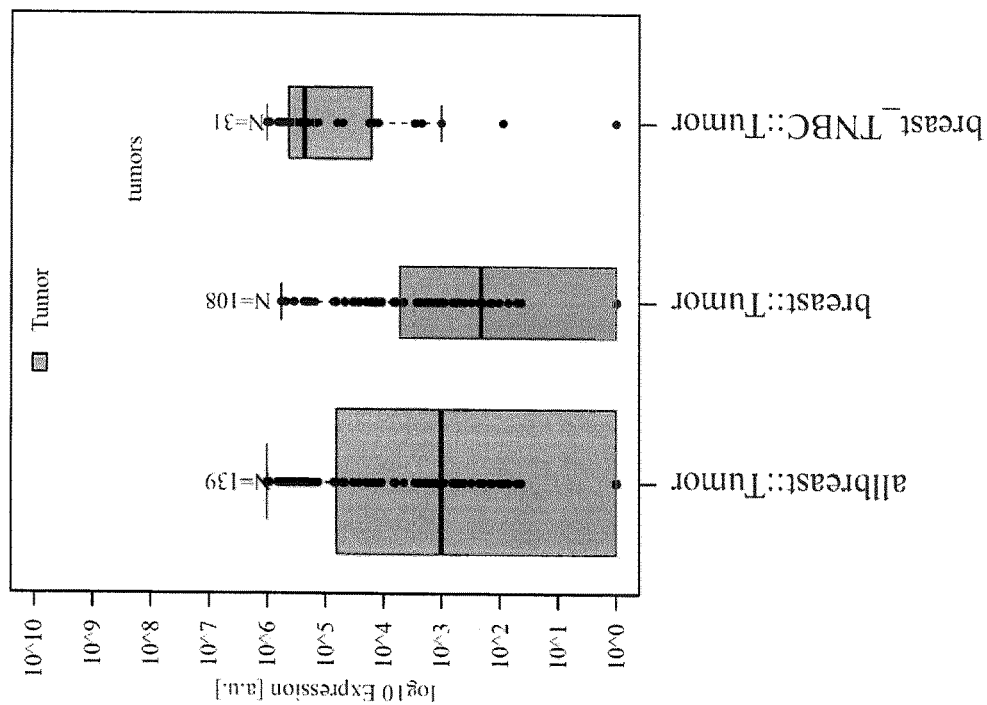
Figure 3B:
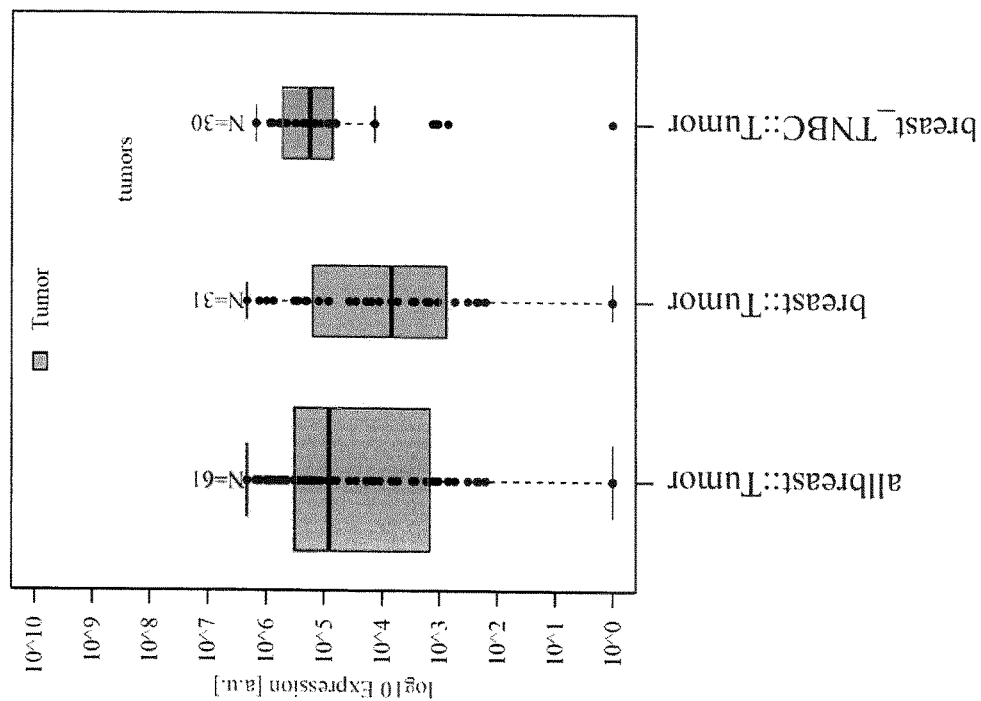
Figure 3C:
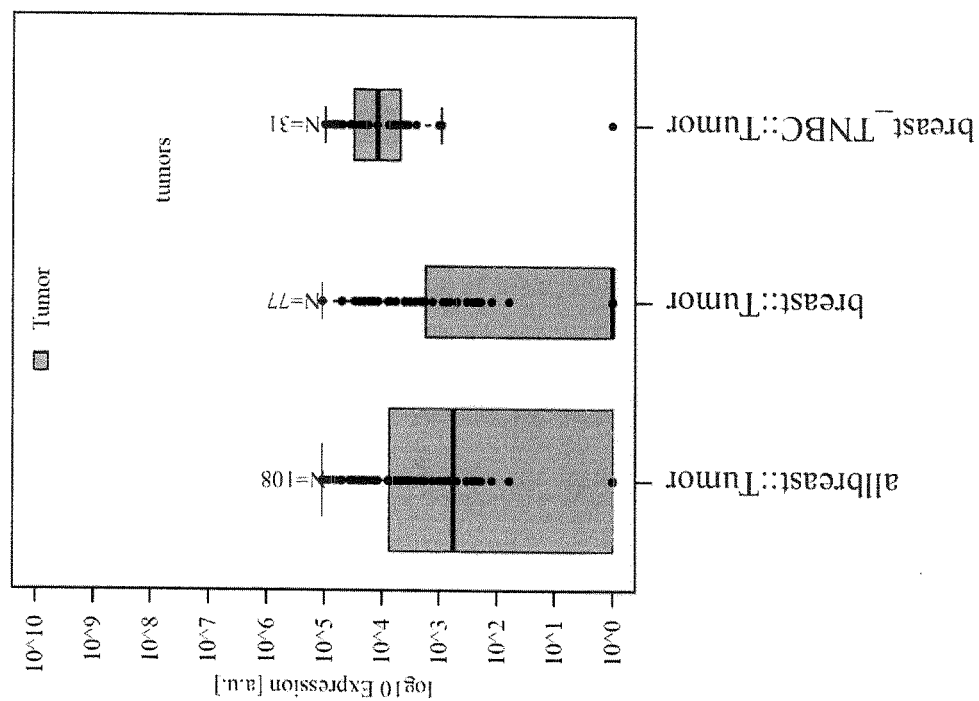

FIG. 3: Box-Whiskers-Plot showing the distribution of transcripts in breast cancer samples Distribution of transcripts for CXORF61 (FIG. 3A), PRAME (FIG. 3B), and CAGE1 (FIG. 3C) is shown irrespectively of the subtype (allbreast:tumor), in the breast cancer samples without the TNBC subtype (breast:tumor) and the TNBC subtype.

Figure 4:
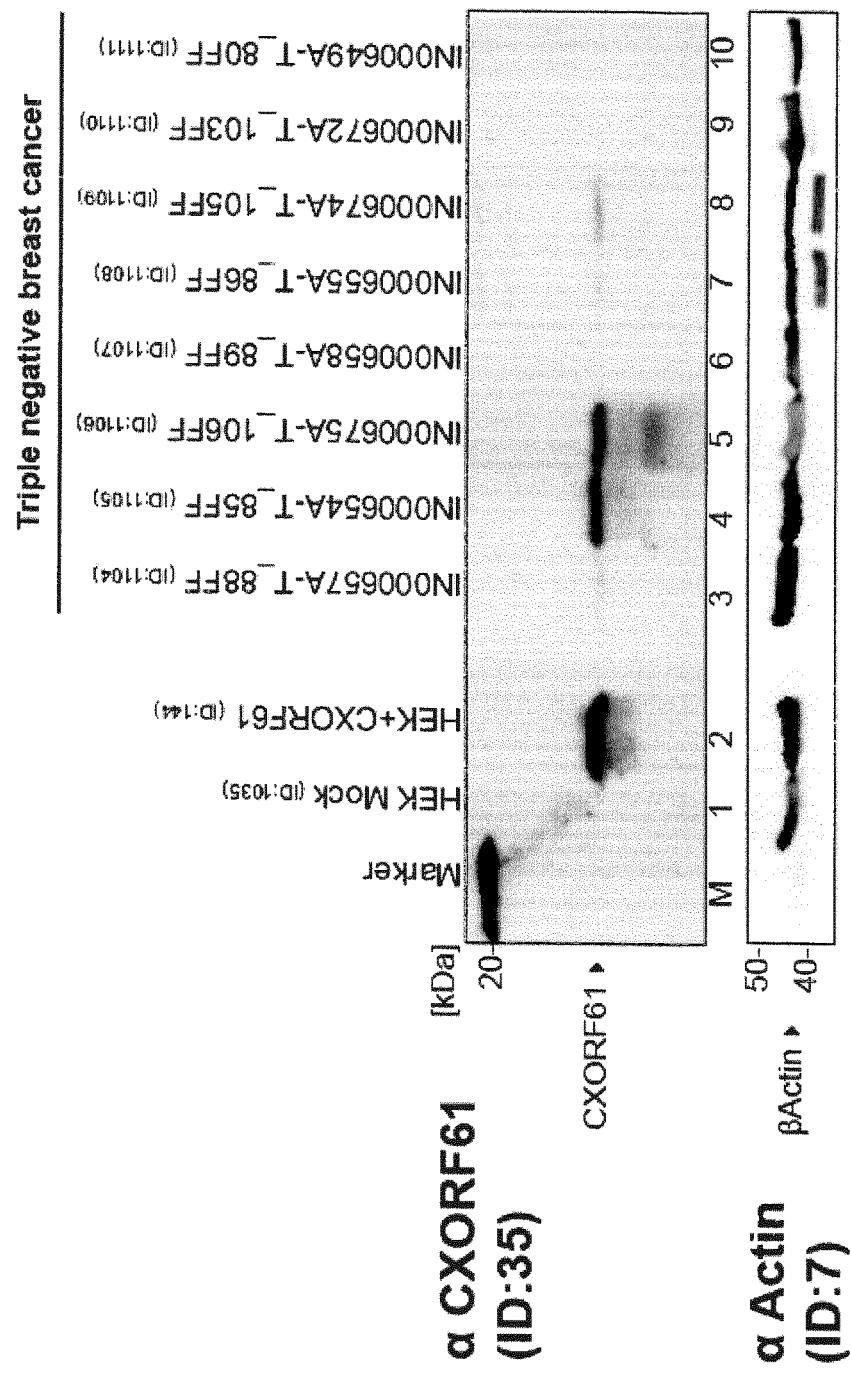

FIG. 4: Expression of CXORF61 on the protein level

Figure 5:
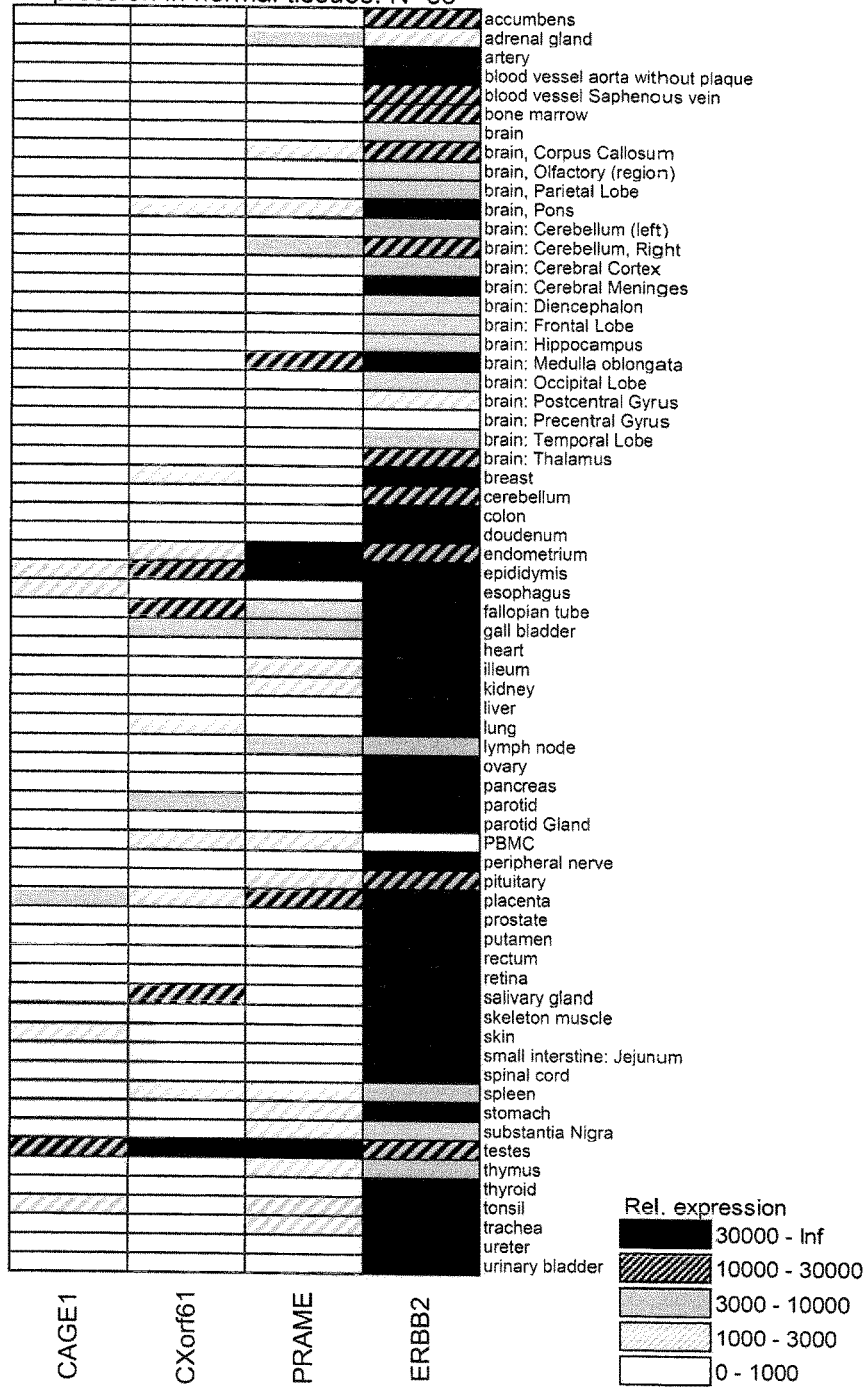

FIG. 5: Tumor specificity of CXORF61, CAGE1 and PRAME

FIG. 6: Identification of T cell epitopes for CXORF61

Figure 7:
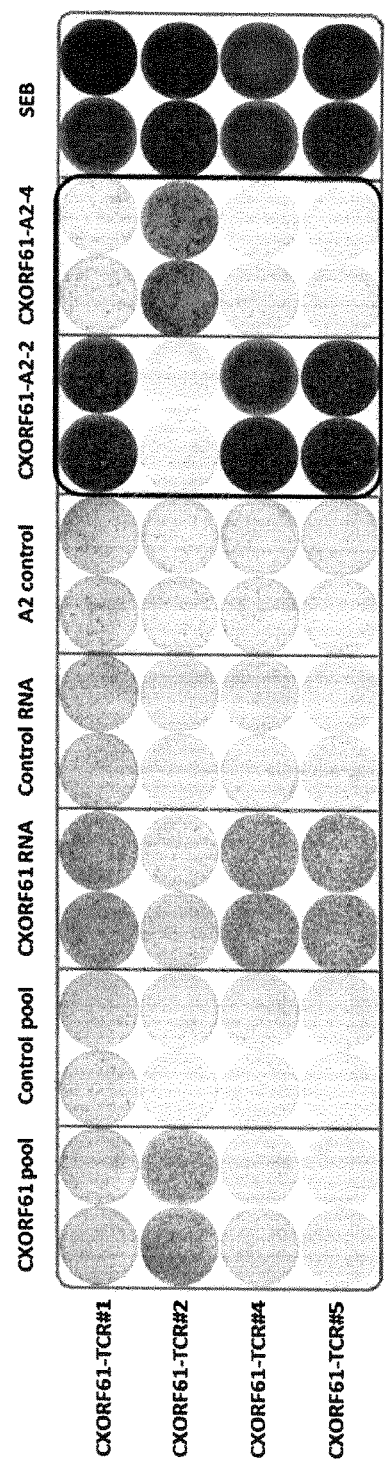

FIG. 7: Testing of T cell receptors for specificity with T cell epitopes for CXORF61

FIG. 8: CXorf61 transcript sequence predicted from NGS analysis

The known CXorf61 sequence (NM_001017978.3) is indicated. The new predicted sequence is in bold.

Figure 9:
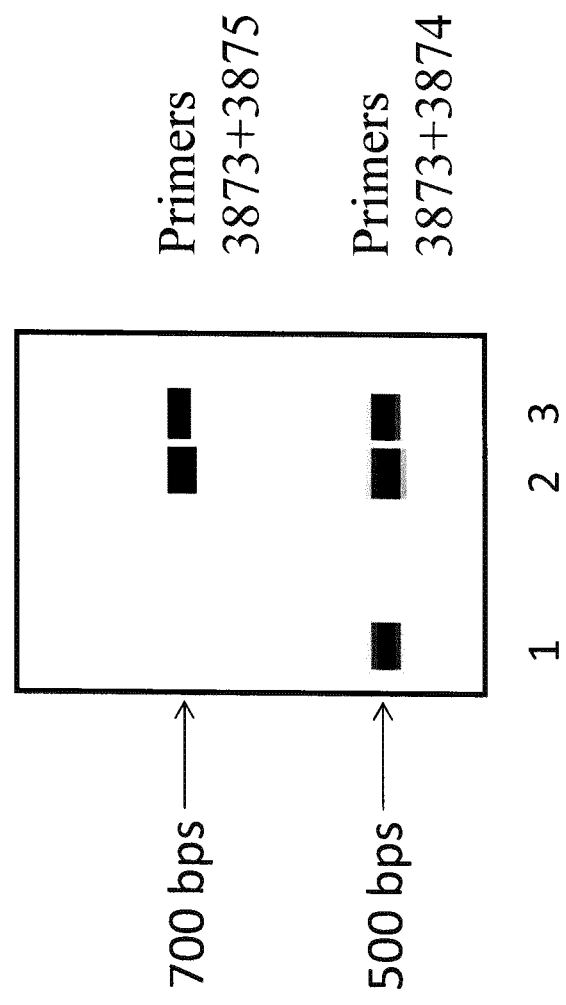

FIG. 9: The existence of the CXorf61-iso1 transcript can be confirmed by PCR

RT-PCR analysis was performed with the indicated primers (for primer sequences see Table 1) using the following cDNAs: 1 Normal testis, 2 MDA-MB468, 3 MDA-MB231.

Figure 10:
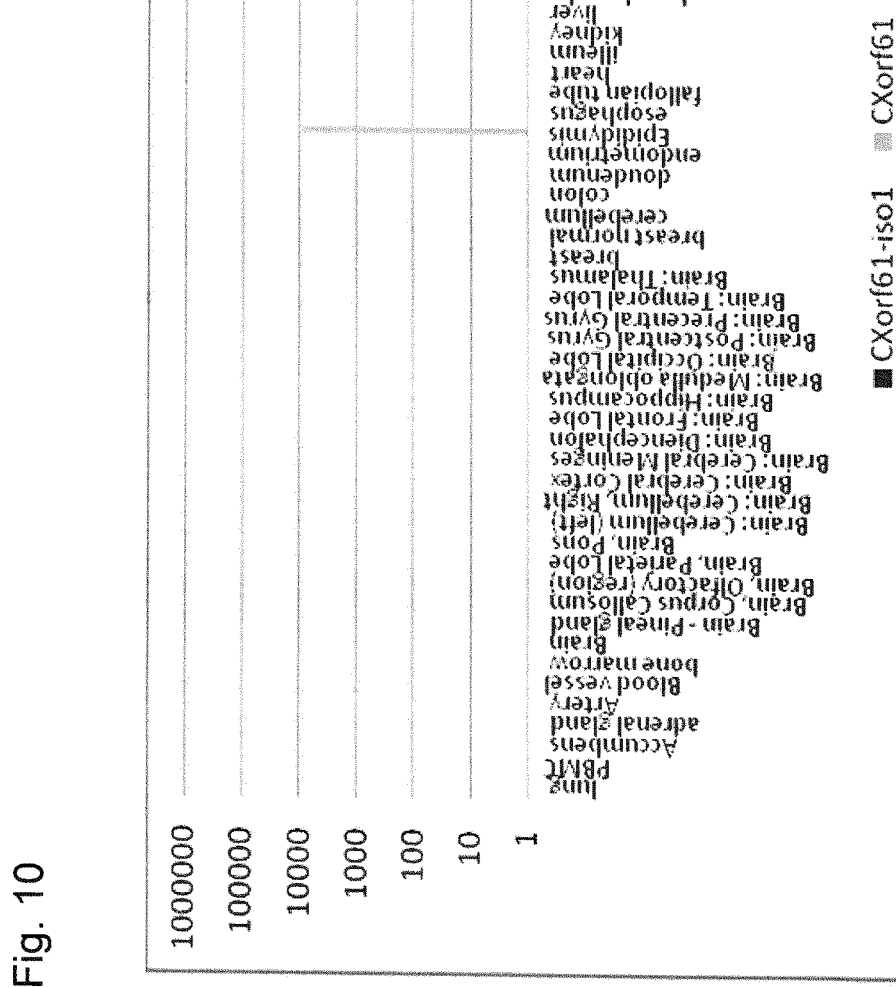

FIG. 10: CXorf6-iso1 is not expressed in normal tissues

The indicated normal tissues (n=65) were analysed by qRTPCR with primers specific for CXorf61 or CXorf61-iso1. Relative expression was calculated with the ΔΔCt method using HPRT as housekeeping gene.

Figure 11:
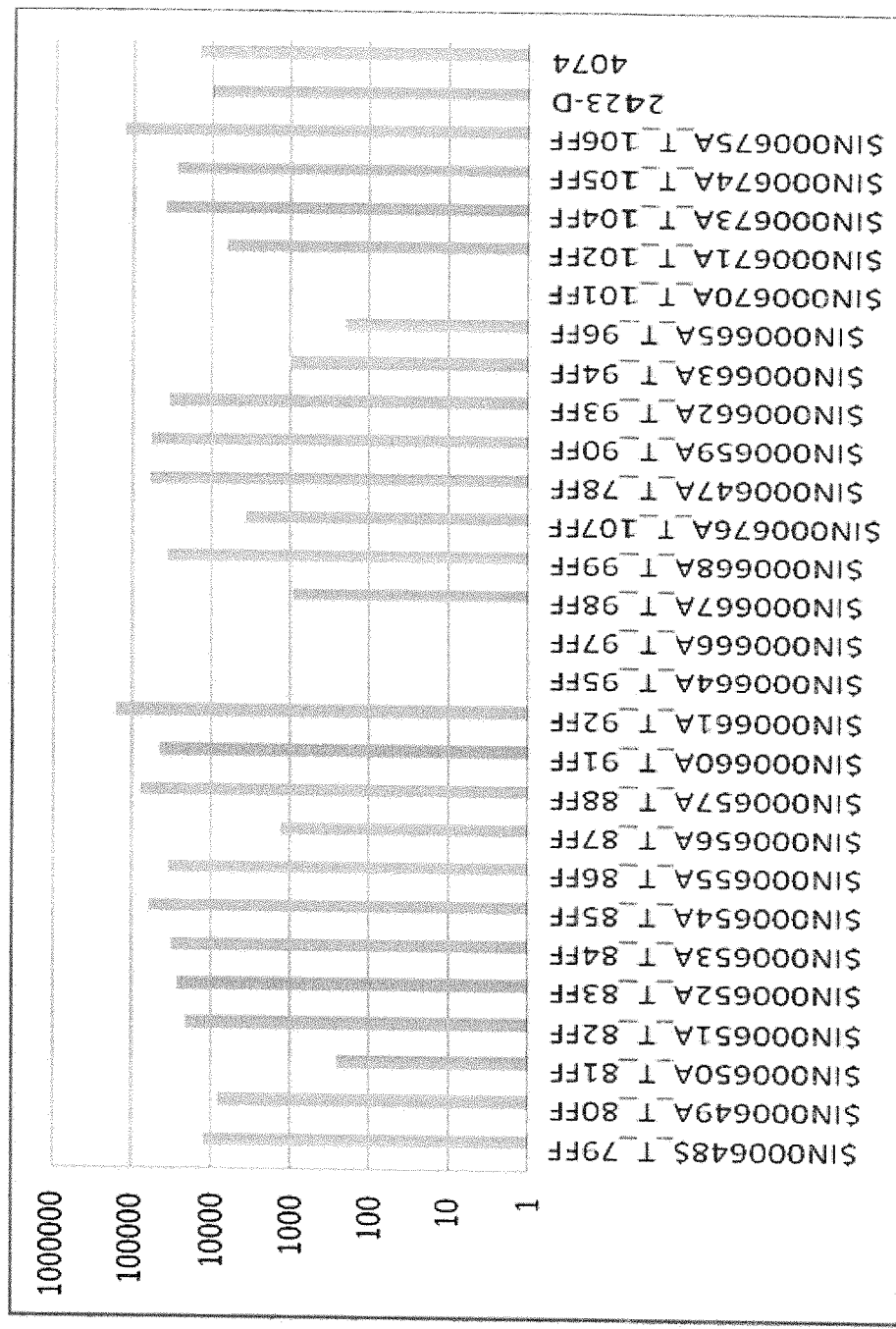

FIG. 11: CXorf61-iso1 is expressed in triple negative breast cancer tissues 29 triple negative breast cancer tissues were analysed by qRT-PCR with primers specific for CXorf61-iso1. Relative expression was calculated with the ΔΔCt method using HPRT as housekeeping gene.

Figure 12:
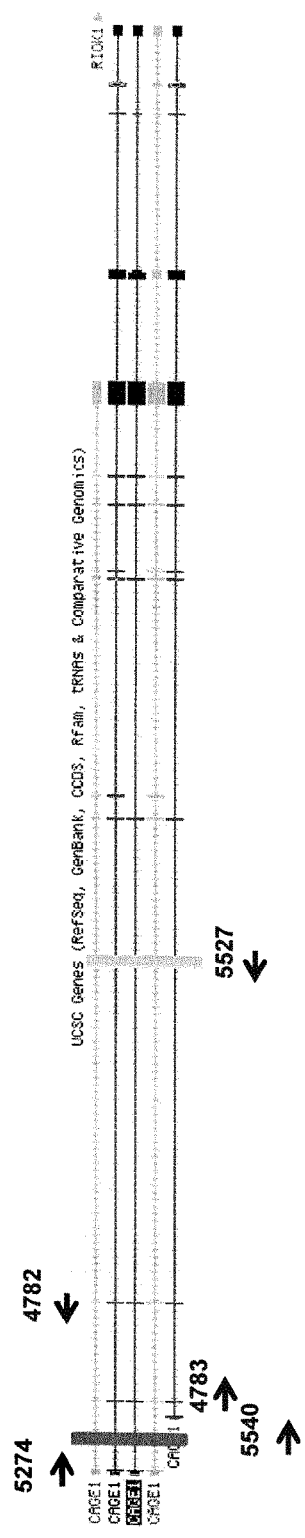

FIG. 12: Positions of the new identified CAGE1 exons

As reference the CAGE1 structure as described in UCSC was used. The position of the primers used for expression analysis is shown, SEQ ID NO: 45 [NEW EXON 1]: light grey, SEQ ID NO: 46 [NEW EXON 2], dark grey FIG. 13: Expression of new CAGE1 isoforms in normal tissues Expression of CAGE1-Tron1 (black columns) and CAGE1-Tron2 (grey columns) was analysed by qRT-PCR with primers 5527+4783 and primers 4782+5540 respectively in the indicated normal tissues. A positive tumor tissue was used as control. Relative expression was calculated with the ΔΔCt method using HPRT as housekeeping gene.

Figure 14:
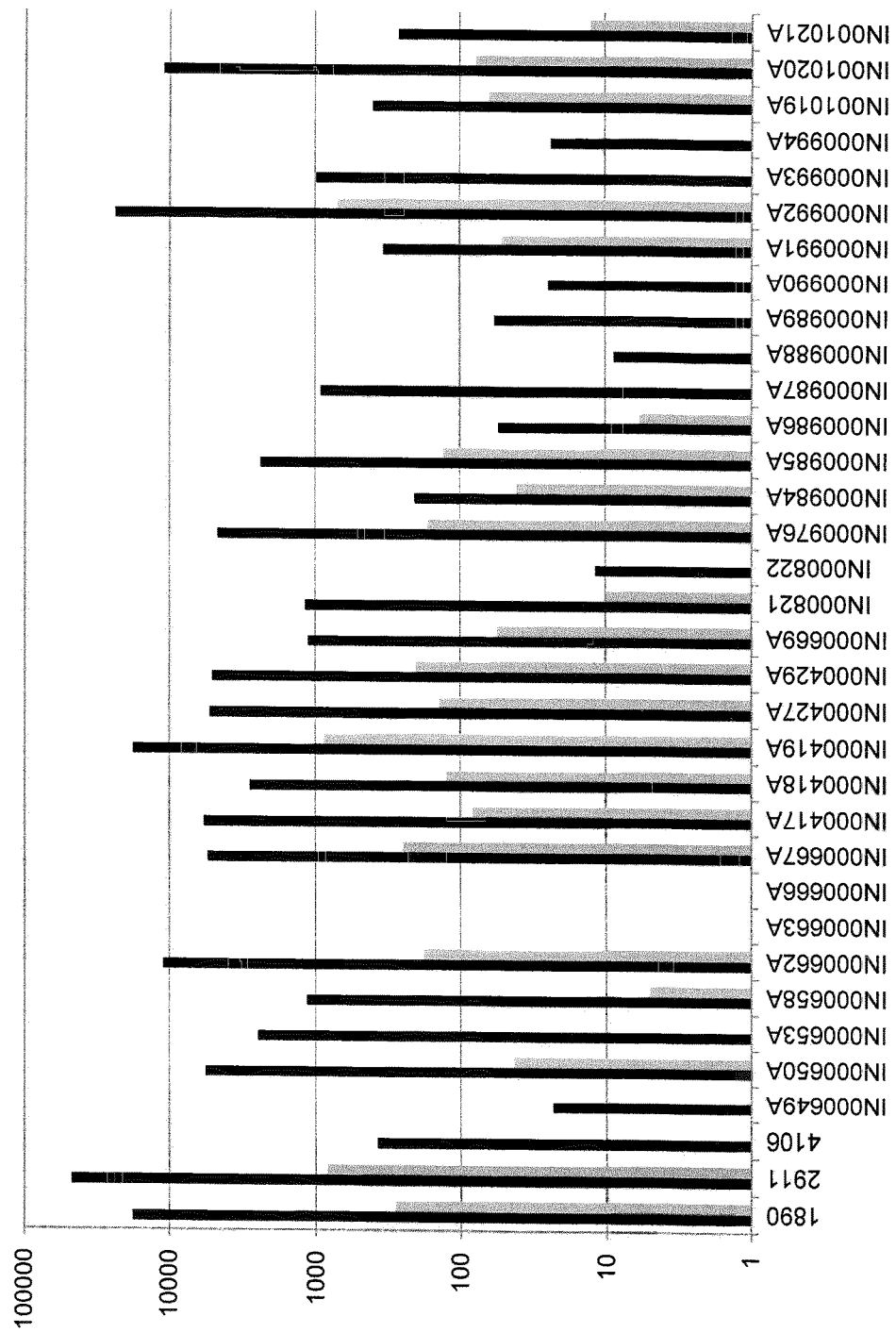

FIG. 14: Expression of new CAGE1 isoforms in cancer tissues

34 Tissues from Triple negatives breast cancer patients were analysed by qRT-PCR with primers specific for CAGE1-Tron1 (primers 5527+4783, dark columns) and CAGE1-Tron2 (primers 4782+5540, grey columns) respectively. Relative expression was calculated with the ΔΔCt method using HPRT as housekeeping gene.

EXAMPLES

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Establishing a Set of Tumor Antigens Useful in a Large Fraction of Cancer Patients It was assessed whether it is possible to establish a set of tumor antigens which is shared at least partially by a large fraction of tumor patients and on the basis of which a set of vaccine products applicable to a broad spectrum of cancer patients can be provided.

To this end, RNA was extracted from normal tissues or breast cancer samples using the RNeasy Lipid Tissue Mini Kit (Qiagen). cDNA synthesis was performed using the SuperScript II Reverse Transcriptase Kit (Invitrogen) and oligo-dT. Expression was analysed using the BioMark™ HD System system (Fluidigm) and the relative expression was calculated using HPRT as house keeping gene.

In this manner, the relative expression of several genes could be detected. The % of positive samples, using a threshold of relative expression of 30000, changed depending on whether all breast cancer samples, irrespectively of the subtype (n=35), were analysed (FIG. 1) or only the TNBC (n=61) subtype was analysed (FIG. 2). Particularly the three transcripts PRAME, CXORF61 and CAGE1, are sufficient to represent about 95% of the analysed patient samples in the TNBC group and 35% in the all breast cancer group. The distribution of the three transcripts in the breast cancer samples, irrespectively of the subtype (allbreast: tumor), in the breast cancer samples without the TNBC subtype (breast:tumor) and the TNBC subtype is shown as Box-Whiskers-Plot in FIG. 3A (CXORF61), FIG. 3B (PRAME), FIG. 3C (CAGE1).

FIG. 4 shows expression of CXORF61 also on the protein level. For the analysis, total protein extracts were generated from 8 human TNBC samples and normalized to β-actin (FIG. 4, lowest panel). CXORF61 expression was analyzed by immunoblotting with a specific antibody (FIG. 4, upper panel). A negative cell lines (Hek-mock) and a positive cell line, Hek transfected with a plasmid coding for CXORF61 (Hek-CXORf61) were used as control. CXORF6 is detectable in 5 out of 8 tested triple-negative breast cancer samples (FIG. 4, lanes 3-5, 7-8).

Example 2: Analysis of Tumor Specificity of CXORF61, CAGE1 and PRAME

The tumor specificity of the three transcripts was analysed by qRT-PCR in a large set of normal tissues (n=65). As shown in FIG. 5, high expression (>30.000) of CXORF61 was detectable only in testis, high expression of PRAME was detectable in testis, endometrium and epididymis. CAGE1 shows only weak expression in testis. In contrast, Erbb2, a generally accepted target for vaccination and other immunotherapeutic approaches, shows a high expression in several normal tissues.

Example 3: T Cell Epitopes of CXORF61, CAGE1 and PRAME

Figure 6B:
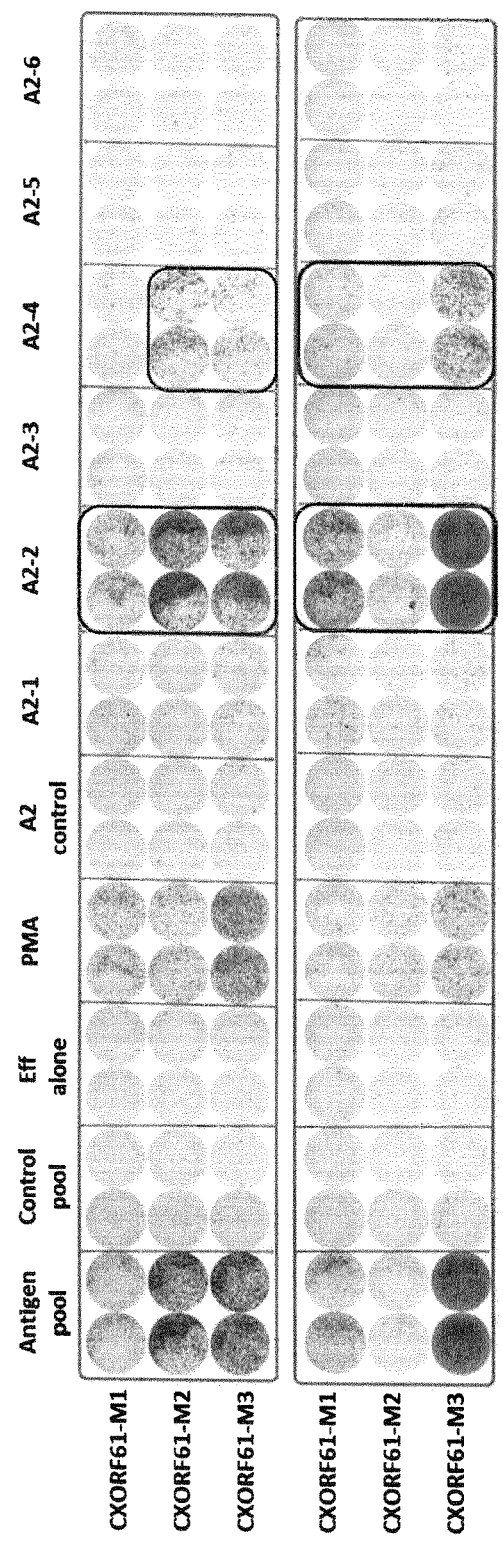

For CXORF61, TCR epitopes were identified by ex-vivo reactivity, analyzed by IFNγ-ELISPOT assay, of spleen cells from CXORF6 immunized HLA-A*02-transgenic mice against CXORF61-derived peptides. To this end, HLA-A*02 binding peptides derived from CXORF61 were predicted applying the SYFPEITHY algorithm (FIG. 6A). Spleen cells were analyzed for reactivity against CXORF61 peptide pool or predicted HLA-A*02-binding CXORF61-derived peptides A2-1-6 (FIG. 6B). Positive control: PMA-treated spleen cells; negative control: an irrelevant peptide pool (HIV-gag), irrelevant nonamer peptide (PLAC1-31-39). Two A2-restricted epitopes were identified (peptide A2-2 and A2-4).

After isolation of TCRs from CD8+ T cells of CXORF61-immunized mice, CD8+ T cells of a HLA-A*02-positive healthy donor were transfected with TCR-α/β chain RNAs and tested by IFNγ-ELISPOT assay for recognition of K562-A2 cells transfected with CXORF61 RNA or pulsed with CXORF61 overlapping 15mer peptides (=CXORF61 pool) or HLA-A*02 binding peptides CXORF61-A2-2/4 (FIG. 7). Negative controls: irrelevant peptide pool (HIV-gag), irrelevant 9mer peptide (Plac1-31-39); Positive control: SEB. Three TCRs were specific for peptide A-2 and one TCR for peptide A2-4.

For PRAME a large number of T cell epitopes has been reported to elicit antitumoral cytotoxic T cell responses. In a publication by Kessler et al. (2001, J. Exp. Med. 193(1): 73-88) four HLA-A*0201-presented cytotoxic T lymphocyte (CTL) PRAME epitopes (VLDGLDVLL, SLYSFPEPEA, ALYVDSLFFL, and SLLQHLIGL) are reported. The publication demonstrated the lysis of mammary carcinoma cell lines for these epitopes. Further PRAME epitopes eliciting a immune response by cytotoxic T lymphocytes have been identified by Kessler et al. (2003, Hum Immunol. 64(2):245-55) (LPRELFPPL, LPRRLFPPLF, FPPLFMAAF, IPVEVLVDLF, LPTLAKFSPY, CPHCGDRTFY, EPILCPCFM, HLA-B35), Kawahara et al. (2006, Exp Hematol. 34(11):1496-504) (GQHLHLETF, HLA-B*62), and Quintarelli et al. (2011, Blood 117(12):3353-62) (NLTHVLYPV, HLA-A*02).

For CAGE1 a publication about serological analysis of cDNA expression libraries (SEREX) showed that cancer patients specifically developed auto-antibodies against this target (Park et al., 2003, Biochim Biophys Acta. 1625(2): 173-82). Induction of cytolytic T lymphocyte (CTL) reactions has been reported for several cancer/testis antigens.

Example 4: Identification of a CXorf61 Isoform Strictly Expressed in Tumor Tissues A new CXorf61 transcript was identified by Next Generation Sequencing, which is expressed in tumor cell lines but not in normal testis. This sequence has a longer 3' UTR and does not change the CXorf61 Open Reading Frame (ORF) (FIG. 8).

To confirm the existence of a longer CXorf61 transcript, the predicted sequence was amplified using primers binding at the 5' of the known sequence and in the new predicted 3' (primers 3873+3875) (FIG. 9). As control, primers binding in NM_001017978.3 were used (primers 3873+3874). While the NM_001017978.3 sequence can be detected in normal testis and breast tumor cell lines MDA-MB468 and MDA-MB231, the new sequence can be detected only in the breast tumor cell lines. The PCR product was sent to sequencing, confirming the existence of the predicted sequence.

Relative expression of CXorf61-iso1 was analyzed by qRT-PCR using the Fluidigm system (primers 2898+3876). While expression of CXorf61 (primers 2898+2899) was detectable very strongly in normal testis and weakly in epididymis and placenta, only irrelevant expression in normal testis was found for CXorf61-iso1 (FIG. 10).

Relative expression of CXorf61-iso1 was analyzed by qRT-PCR using the Fluidigm system in triple negative breast cancer patient samples with primers 2898+3876 (FIG. 11). Using a threshold of 10000, 59% of the samples were positive for CXorf61 iso1.

TABLE 1

Sequence of the primers used

| Primer | Sequence (5'-3') |
|---|---|
| 3873 | CCGTTTCCCAAATCCAGGC |
| 3874 | ATCTACTCAAAGTGTCTTTAATGATTTCC |
| 2898 | GTGTGCCTTGATTGTCTTCTGG |
| 3875 | CTTTCTCTATTGTGCTTCCATTCC |
| 3876 | GTATCTGGATTTTTTGTATGTGACTTGGAAT |
| 2899 | CCTGGCTATTGAGTGTGGG |

Example 5: Identification of CAGE1 Isoforms Strictly Expressed in Tumor Tissues By using Next Generation sequencing an alternative start codon in the CAGE1 sequence was identified. The existence of the new exon was confirmed by RT-PCR and sequencing. RT-PCR analysis was performed with primers 5274 and 5527 (for primers sequence see Table 2, for primers position see FIG. 12) using the cDNA of a Triple negative breast cancer patient. The amplified products were extracted from the gel and were sequenced.

TABLE 2

Sequence of the primers used for expression analysis

| Primer number | Sequence (5'-3') |
|---|---|
| 5274 | GACTCTTCCTGGAGTGGTTGA |
| 5540 | GAACCCCGGAAGTGGAGGTT |
| 4783 | GGTCATGGACTTCGGATGATT |
| 4782 | AGGATTTAATTAGAAAGCCCAGAGA |
| 5527 | CTCTACCCCTGTATTTCGCTTG |

The position of the primers used for expression analysis is shown in FIG. 12. The light grey bar indicates the exon at 5' and the dark grey bar the exon at 3' of the same figure. The new isoforms are shorter as the known CAGE1 isoforms. The new identified CAGE1 isoforms are SEQ ID NO: 41 [CAGE1-TRON1] and 42 [CAGE1-TRON2] encoding for the predicted ORFs of SEQ ID NO: 43 [CAGE1-TRON1-ORF] and 44 [CAGE1-TRON2-ORF], respectively. CAGE1-TRON1 comprises the new exon of SEQ ID NO: 45 and CAGE1-TRON2 comprises the new exons SEQ ID NO: 45 and 46. As reference the CAGE1 structure as described in UCSC was used:

TABLE 3

CAGE1 reference sequences

CAGE1 (uc021y1c.1) at chr6: 7326887-7389942-*Homo sapiens* cancer antigen 1 (CAGE1), transcript variant 3, mRNA.
CAGE1 (uc003mxl.2) at chr6: 7326887-7389942-*Homo sapiens* cancer antigen 1 (CAGE1), transcript variant 1, mRNA.
CAGE1 (uc003mxk.2) at chr6: 7329330-7389942-*Homo sapiens* cancer antigen 1 (CAGE1), transcript-variant 2, mRNA,
CAGE1 (uc003mxj.3) at chr6: 7326887-7389942-*Homo sapiens* cancer antigen 1 (CAGE1), transcript variant 1, mRNA.
CAGE1 (uc003mxh.3) at chr6: 7326887-7374364-*Homo sapiens* cancer antigen 1 (CAGE1), transcript variant 1, mRNA.

Figure 13:
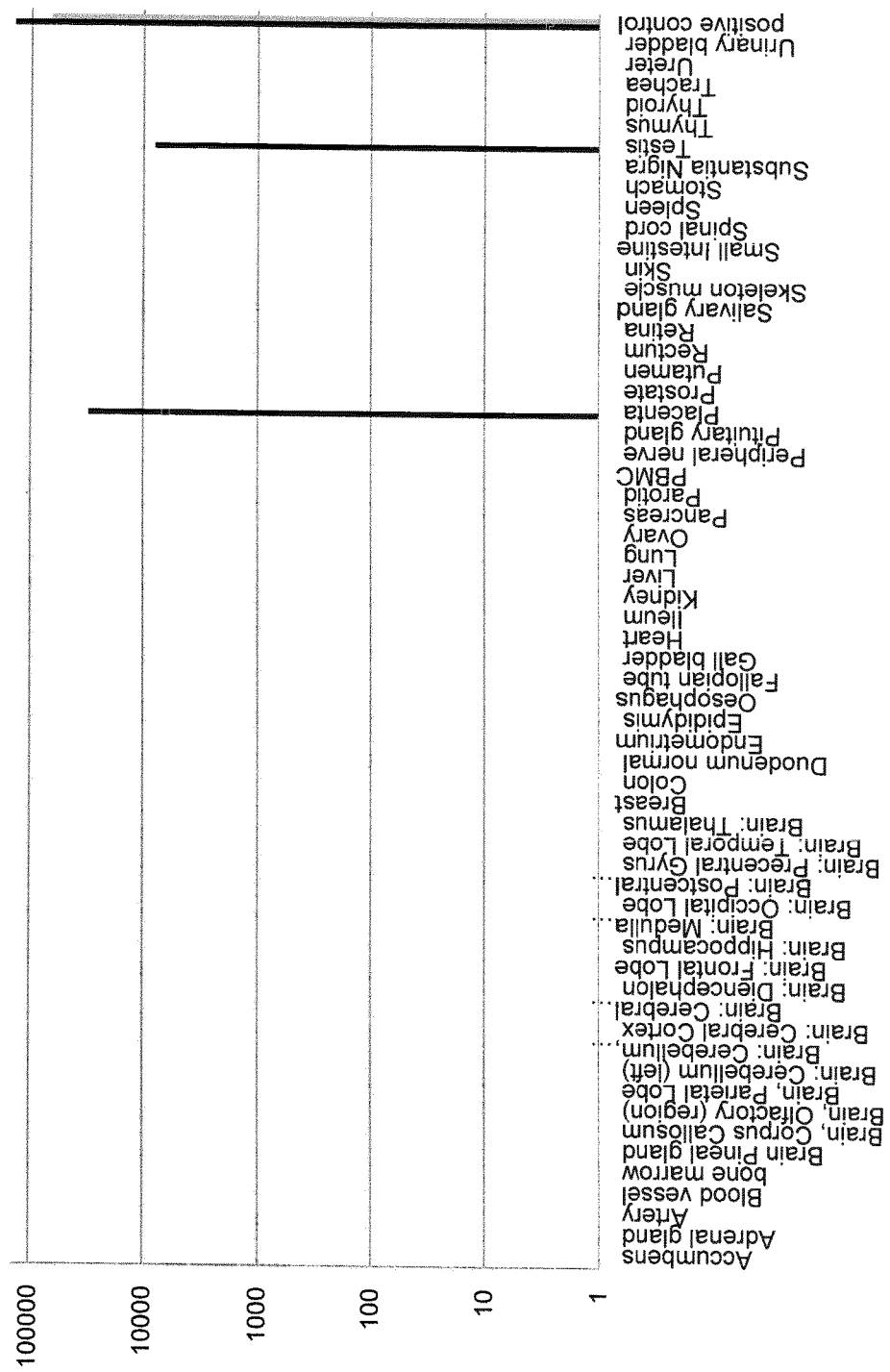

CAGE1-Tron1 and CAGE1-Tron2 have a restricted expression in normal tissues. Relative expression of CAGE1-Tron1 and CAGE1-Tron2 was analysed in 60 normal tissues, including several brain areas by qRT-PCR using the Fluidigm technology. Expression of CAGE1-Tron1 was detected in placenta and at less extent in testis. No expression of CAGE1-Tron2 was detected in any normal tissues (FIG. 13).

CAGE1-Tron1 and CAGE1-Tron2 are expressed in Triple negative breast cancer tissues. Relative expression of CAGE1-Tron1 and CAGE1-Tron2 was analyzed by qRT-PCR in 34 triple negative breast cancer patient samples. Using a cut off of 100, 73% of the tumors are positive for CAGE1-Tron1 and 32% for CAGE1-Tron2 (FIG. 14).

The invention claimed is:

1. A method for treating triple negative breast cancer in a patient comprising
   a) detecting the expression pattern of a set of tumor antigens in a sample from the patient, wherein the set of tumor antigens comprises CXorf61, CAGE1, and PRAME;
   b) diagnosing the patient as needing a cancer therapy regimen when CXorf61, CAGE1, and PRAME are expressed; and
   c) treating the patient with an immunotherapeutic that targets the set of tumor antigens expressed in the patient.

2. The method of claim 1 wherein the sample comprises cancer cells.

3. The method of claim 1 wherein detecting the expression pattern comprises a quantitative and/or qualitative determination of the expression of the tumor antigens.

4. The method of claim 1 wherein detecting the expression pattern comprises determining the expression of RNA and/or protein of the tumor antigens.

5. A method for treating triple negative breast cancer in a patient comprising administering to said patient an immunotherapeutic targeting each tumor antigen of a set of tumor antigens, wherein the set of tumor antigens comprises CXorf6, CAGE1, and PRAME.

6. The method of claim 5 which comprises inducing a cellular immune response in the patient against each tumor antigen of the set of tumor antigens.

7. The method of claim 6 wherein the cellular immune response is induced by administering a vaccine providing one or more T cell epitopes of each tumor antigen of the set of tumor antigens to the patient.

* * * * *